United States Patent
Leibowitz et al.

(10) Patent No.: US 10,028,924 B2
(45) Date of Patent: Jul. 24, 2018

(54) ANTIMICROBIAL COMPOSITIONS

(71) Applicant: DeLaval Holding AB, Tumba (SE)

(72) Inventors: Sarah Leibowitz, Kansas City, MO (US); N. Camelia Traistaru, Kansas City, MO (US)

(73) Assignee: DeLaval Holding AB, Tumba (SE)

( * ) Notice: Subject to any disclaimer, the term of this patent is extended or adjusted under 35 U.S.C. 154(b) by 0 days.

(21) Appl. No.: 15/031,036

(22) PCT Filed: Oct. 22, 2014

(86) PCT No.: PCT/SE2014/051242
§ 371 (c)(1),
(2) Date: Apr. 21, 2016

(87) PCT Pub. No.: WO2015/060775
PCT Pub. Date: Apr. 30, 2015

(65) Prior Publication Data
US 2016/0263062 A1    Sep. 15, 2016

Related U.S. Application Data

(60) Provisional application No. 61/895,232, filed on Oct. 24, 2013.

(51) Int. Cl.
| | | |
|---|---|---|
| *A01N 37/00* | (2006.01) | |
| *A61K 31/19* | (2006.01) | |
| *A01N 37/36* | (2006.01) | |
| *A61K 9/00* | (2006.01) | |
| *A61K 47/10* | (2017.01) | |
| *A61K 47/20* | (2006.01) | |

(52) U.S. Cl.
CPC .............. *A61K 31/19* (2013.01); *A01N 37/36* (2013.01); *A61K 9/0041* (2013.01); *A61K 47/10* (2013.01); *A61K 47/20* (2013.01)

(58) Field of Classification Search
CPC .... A01N 37/36; A01N 2300/00; A01N 25/30; A61K 31/19; A61K 47/10; A61K 47/20; A61K 9/0041
USPC ......................................................... 514/557
See application file for complete search history.

(56) References Cited

U.S. PATENT DOCUMENTS

| | | | | |
|---|---|---|---|---|
| 4,891,216 | A | 1/1990 | Kross et al. | |
| 7,109,241 | B1 | 9/2006 | Richter et al. | |
| 7,662,238 | B2 * | 2/2010 | Garner | C11D 3/044 134/14 |
| 8,153,613 | B2 | 4/2012 | Ahmed et al. | |
| 8,569,373 | B2 * | 10/2013 | Foret | A01N 37/02 514/557 |
| 8,772,341 | B2 | 7/2014 | Foret et al. | |
| 8,778,369 | B2 | 7/2014 | Ahmed et al. | |
| 8,865,196 | B2 * | 10/2014 | Omidbakhsh | A01N 37/36 424/405 |
| 8,871,807 | B2 * | 10/2014 | Gohl | A01N 41/04 514/2.3 |
| 9,750,755 | B2 * | 9/2017 | Ahmed | A61K 31/60 |
| 2003/0206882 | A1 | 11/2003 | Richter et al. | |
| 2010/0234328 | A1 | 9/2010 | Ahmed et al. | |
| 2010/0234460 | A1 | 9/2010 | Foret et al. | |
| 2015/0272969 | A1 * | 10/2015 | Ahmed | A01N 37/02 514/159 |
| 2015/0335598 | A1 * | 11/2015 | Buchalova | A61K 9/0017 514/574 |

FOREIGN PATENT DOCUMENTS

| | | |
|---|---|---|
| CA | 1244759 | 11/1988 |
| GB | 2398571 | 8/2004 |
| WO | 2008031087 | 3/2008 |
| WO | 2014098759 | 6/2014 |
| WO | WO 2014098759 A1 * | 6/2014 ........... A61K 9/0017 |

OTHER PUBLICATIONS

The International Search Report and Written Opinion dated Jan. 14, 2015, in PCT/SE2014/051242 filed on Oct. 22, 2014.
The Examination Report No. 1 dated Jul. 21, 2017, in AU application No. 2014337749.
Clear Pore Acne Wash Professional Strength, http://www.gnpd.com/sinatra/recordpage/1590868>, published Jul. 2011 according to Mintel GNDP, http://www.hollywoodstyleusa.com/acne_treatment/clear_pore_acne_wash.html.

* cited by examiner

*Primary Examiner* — My-Chau T. Tran
(74) *Attorney, Agent, or Firm* — Hovey Williams LLP

(57) ABSTRACT

Antimicrobial compositions and related methods are disclosed. The antimicrobial compositions include glycolic acid, an anionic surfactant, and at least one additional surfactant selected from anionic and nonionic surfactants.

12 Claims, No Drawings

ANTIMICROBIAL COMPOSITIONS

RELATED APPLICATIONS

The present application is a national stage entry under 35 U.S.C. 371 of International Patent Application No. PCT/SE2014/051242, filed Oct. 22, 2014, which claims the benefit of U.S. Provisional Patent Application Serial No. 61/895,232, filed Oct. 24, 2013, both of which are incorporated by reference herein in their entireties.

BACKGROUND

1. Field of the Invention

The present invention pertains to antimicrobial compositions. More particularly, the present invention is directed toward antimicrobial compositions that can control or destroy pathogenic microorganisms in a wide variety of applications.

2. Description of the Related Art

Antimicrobial agents are generally used to reduce the risk of infection for humans or animals, for example, by disinfecting surfaces in various food or medical related areas, or by controlling pathogenic organisms on skin. Antimicrobial agents may also be used in veterinary applications, for example, to control and prevent hoof diseases, mastitis, or topical infections. Prevention of mastitis is a major goal of the dairy industry, where the disease may result from the contact of the bovine or ovine mammary gland with pathogenic microorganisms. Mastitis is a potentially serious infection, where severe cases can cause the death of a dairy animal.

To reduce mastitis, commercial teat dips have been developed that are generally administered to the teat by dipping, spraying, or foaming the teat prior to, and after, milking. Commercially available teat dips may be divided into two primary classifications, namely, barrier and non-barrier dips. The non-barrier teat dips are strictly antimicrobial and are applied to kill microorganisms that are already present in the teat canal or on the surface of the teat skin. By design, the antimicrobial effect is substantially immediate, targeting the contagious organisms that may be transferred between animals during the pre-milking, milking and post-milking process. The barrier dips may also be antimicrobial and are applied to form a prophylactic film or coating that may prevent microbes from contacting the teat.

Current commercial teat dips can be problematic in that they may contain active agents, such as iodine, hypochlorite, chlorine dioxide, chlorhexidine, and hypochlorous acid, which can be noxious to both humans and the dairy animal. Additionally, the use of overly powerful disinfectants, such as hypochlorite, may contribute to the problem of mastitis in that these agents can cause irritation to the teat skin. While there are milder antimicrobial agents available, such agents do not provide a broad spectrum of protection.

In addition, the antimicrobial agents used in various current commercial teat dips can be problematic from a consumption stand point. For example, small quantities of iodine and chlorhexidine can result in changes to the milk. Further, food and drug regulations take into consideration the potential for the ingestion of residual teat dip agents. This is especially problematic with chlorhexidine, which is synthetic and is not a natural component of food or milk. Also, iodine is associated with problems of staining, and some operators/users develop allergic symptoms such as skin irritation and sensitization from iodine-based product use.

Therefore, there is a need for antimicrobial compositions that offer protection against a broad spectrum of microbes and are non-irritating to the skin.

SUMMARY

In one embodiment of the present invention there is provided an antimicrobial composition that includes glycolic acid, an anionic surfactant, and a nonionic surfactant.

In another embodiment of the present invention there is provided a method for controlling or preventing bovine mastitis. The method includes contacting the teats of a cow with a teat dip, which includes glycolic acid, an anionic surfactant, and a nonionic surfactant. The teat dip is characterized by a Lysis/Denaturation (L/D) ratio greater than 100.

In yet another embodiment of the present invention there is provided an antimicrobial composition that includes glycolic acid, sodium octane sulfonate or sodium lauryl sulfate, and at least one additional surfactant. The additional surfactant is selected from anionic surfactants, nonionic surfactants, and mixtures thereof.

In another embodiment of the present invention there is provided a method for controlling or preventing bovine mastitis. The method includes contacting the teats of a cow with a teat dip, which includes glycolic acid, sodium octane sulfonate or sodium lauryl sulfate, and at least one additional surfactant. The additional surfactant is selected from anionic surfactants, nonionic surfactants, and mixtures thereof. The teat dip is characterized by a Lysis/Denaturation (L/D) ratio greater than 100.

DETAILED DESCRIPTION

Various embodiments of the present invention concern antimicrobial compositions that include an organic acid, an anionic surfactant, and a nonionic surfactant.

As used herein, the term "organic acid" means an organic compound that is an acid. The most common examples are the carboxylic acids having an acidity that derives from a carboxyl group —COOH. Other groups may also impart weak acidity, especially hydroxyl (—OH) groups, thiol (—SH) groups, enol groups (—C=C(OH)—), sulfate groups (—OSO$_3$H), sulfonate groups (—SO$_3$H) and phenols. Preferred organic acids have a carbon number less than twenty, and this number is even more preferably less than ten. The organic acids may be aliphatic, aryl, aromatic, unsubstituted or substituted with functional groups. The substituent(s) may be attached to any position of the carbon chain or carbon ring.

In certain embodiments, the organic acid may include lactic acid, salicylic acid, tartaric acid, citric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, oxalic acid, glutamic acid, adipic acid, hexanoic acid, octanoic acid, nonanoic acid, decanoic acid, undecanoic acid and combinations thereof. In certain other embodiments, inorganic acids having pK$_a$ characteristics approximating those of organic acids may also be used, such as, sulfamic acid. In one or more embodiments, glycolic acid is a particularly preferred organic acid for use in the present invention. In certain embodiments, glycolic acid is the only organic acid present in the compositions of the present invention.

Anionic surfactants suitable for use in the present invention include, but are not limited to, alkyl sulfonates, secondary alkane sulfonates, alkyl sulfates, alkyl ether sulfates, aryl sulfonates, aryl sulfates, alkylaryl sulfonates, alkylaryl sulfates and alkyl ether sulfonates, and the corresponding acids thereof. A non-limiting list of specific anionic surfactants suitable for use in the present invention includes: alkali lauryl sulfates, e.g., sodium lauryl sulfate (SLS), alkali dodecylbenzenesulfonates, alkali octane sulfonates, e.g., sodium octane sulfonate (SOS), alkali secondary alkane sulfonates, alkali lauryl ether sulfates and ammonium salts thereof. Additional anionic surfactants may include: a linear alkyl benzene sulfonate, an alkyl α-sulfomethyl ester, an α-olefin sulfonate, an alcohol ether sulfate, an alkylsulfo succinate, and a dialkylsulfo succinate. Specific examples of such additional anionic surfactants are linear C10-C16 alkylbenzene sulfonic acid, linear C10-C16 alkylbenzene sulfonate or alkali metal, alkaline earth metal, amine and ammonium salts thereof, e.g., sodium dodecylbenzene sulfonate, sodium C14-C16 α-olefin sulfonate, sodium methyl α-sulfomethyl ester and disodium methyl α-sulfo fatty acid salts. In certain embodiments, the antimicrobial compositions of the present invention may include a mixture of any of the above listed anionic surfactants. It is within the scope of the present invention that all anionic surfactants disclosed hereto may be in acid form, or in the form of an alkali metal, an alkaline earth metal, an amine, or an ammonium salt. In certain embodiments, it is preferable that compositions according to the present invention do not comprise an α-olefin sulfonate as the only anionic surfactant. In other embodiments when SOS comprises an anionic surfactant, it is preferable that it be used in conjunction with a further surfactant, such as another anionic surfactant, a nonionic surfactant as discussed below, or both another anionic surfactant and a nonionic surfactant.

In one or more embodiments, sodium octane sulfonate is particularly preferred for use as the anionic surfactant in the antimicrobial compositions of the present invention. In certain embodiments, sodium lauryl sulfate is the preferred anion surfactant for use in the antimicrobial compositions of the present invention. In one or more embodiments, alkyl sulfonates are the only anionic surfactants present. For example, in one or more embodiments, sodium octane sulfonate is the only anionic surfactant present. In certain other embodiments, alkyl sulfates are the only anionic surfactants present. For example, in various embodiments, sodium lauryl sulfate is the only anionic surfactant present. In certain embodiments, one or more anionic surfactants can be used. For example, in such embodiments, a mixture of alkyl sulfonates and alkyl sulfates may be used, such as, sodium octane sulfonate and sodium lauryl sulfate.

Nonionic surfactants suitable for use in the present invention include, but are not limited to, alkyl polyglucosides, alkyl ethoxylated alcohols, alkyl propoxylated alcohols, ethoxylated-propoxylated alcohols, sorbitans, sorbitan esters, alkanol amides, ethyleneoxide-propyleneoxide block copolymers, and mixtures thereof. A non-limiting list of specific nonionic surfactants includes a $C_9$-$C_{11}$ alcohol with an average of approximately 8 moles of ethylene oxide per mole of alcohol (Neodol® 91-8 from Shell Chemicals), a $C_8$-$C_{18}$ alcohol with odd or even number carbon chain, with an average of 6 to 18 moles of ethylene oxide per mole of alcohol, alkyl polyglucosides (e.g., Triton™ BG10 from Dow Corp. or Lutensol® GD 70 from BASF Corp.), branched secondary alcohol ethoxylates (e.g., TERGITOL™ TMN Series from Dow Corp.), ethylene oxide/propylene oxide copolymers (e.g., TERGITOL™ L Series from Dow Corp.), secondary alcohol ethoxylates (e.g., ECOSURF™ LF-20 or TERGITOL™ 15-S Series from Dow Corp.), polyether polyols (e.g., TERGITOL™ L-61 from Dow. Corp), nonylphenol ethoxylates (e.g., TERGITOL™ NP Series from Dow Corp.), octylphenol ethoxylates (e.g., TRITON™ X Series from Dow Corp), seed oil surfactants (e.g., ECOSURF™ SA surfactants from Dow Corp.), alkyl polysaccharides (e.g., ALKADET® series from Huntsman Chemicals), alkylamine ethoxylates (e.g., SURFONIC® T series from Huntsman Chemicals), amine oxides (e.g., EMPIGEN® O series from Huntsman Chemicals), block copolymers (e.g., EMPILAN® KCMP series from Huntsman Chemicals), castor oil ethoxylates (e.g., SURFONIC® CO series from Huntsman Chemicals), ceto-oleyl alcohol ethoxylates (e.g., EMPILAN® KLA series from Huntsman Chemicals), ceto-stearyl alcohol ethoxylates (e.g., EMPILAN® KM series from Huntsman Chemicals), decyl alcohol ethoxylates, dinonyl phenol ethoxylates (e.g., SURFONIC® DNP series from Huntsman Chemicals), Dodecyl phenol ethoxylates (e.g., SURFONIC® DDP series from Huntsman Chemicals), end-capped ethoxylates (e.g., TERIC® 165 from Huntsman Chemicals), ethoxylated alkanolamides (e.g., EMPILAN® MAA series from Huntsman Chemicals), ethylene glycol esters (e.g., EMPILAN® EG series from Huntsman Chemicals), fatty acid alkanolamides (e.g., EMPILAN® CD series from Huntsman Chemicals), fatty alcohol alkoxylates (e.g., SURFONIC® LF series from Huntsman Chemicals), lauryl alcohol ethoxylates (e.g., TERIC® 12A series from Huntsman Chemicals), mono-branched alcohol ethoxylates (e.g., EMPILAN® KCA series from Huntsman Chemicals), nonyl phenol ethoxylates (e.g., SURFONIC® N series from Huntsman Chemicals), octyl phenol ethoxylates (e.g., SURFONIC® OP series from Huntsman Chemicals), random copolymer alkoxylates (e.g., HYDROL® series from Huntsman Chemicals), sorbitan ester ethoxylates (e.g., ECOTERIC® T series from Huntsman Chemicals), stearic acid ethoxylates (e.g., TERIC® SF series from Huntsman Chemicals), synthetic alcohol ethoxylates (e.g., EMPILAN® KH series from Huntsman Chemicals), tall oil fatty acid ethoxylates (e.g., TERIC® T series from Huntsman Chemicals), tallow amine ethoxylates (e.g., EMPILAN® AMT series from Huntsman Chemicals), ethoxylates of linear oleochemical alcohols (e.g., Lutensol® A grades from BASF Corp.), oxo alcohol ethoxylates that are based on predominately linear alcohols (e.g., Lutensol® AO grades from BASF Corp.), alkylphenol ethoxylates (e.g., Lutensol® AP grades from BASF Corp.), alkylpolyethylene glycol ethers made from a linear, saturated $C_{16}C_{18}$ fatty alcohol (e.g., Lutensol® AT grades from BASF), a $C_8$-$C_{10}$ alcohol with an average of approximately 6 or 8 moles of ethylene oxide per mole of alcohol (Surfonic® L12-6 or Surfonic® L12-8 from Huntsman Chemicals, respectively), nonylphenoxypoly(ethyleneoxy)ethanol, with a degree of polymerization ranging from 9 to 10 (Surfonic® N-95 from Huntsman Chemicals), a $C_8$-$C_{16}$ alkyl polyglucoside with a degree of polymerization ranging from 1 to 3, e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), or $C_{12}$-$C_{16}$ alkyl polyglucoside with a degree of polymerization of 1.6 (Glucopon® 625), and polyethoxylated polyoxypropylene block copolymers (poloxamers) including by way of example the Pluronic® poloxamers commercialized by BASF Chemical Co. In a preferred embodiment, the nonionic surfactant includes an alcohol ethoxylate, such as Neodol® 91-8 or Surfonic® L12-8. In certain embodiments, an alcohol ethoxylate is the only nonionic surfactant present.

In certain embodiments, the antimicrobial activity of the compositions of the present invention may be due to the presence of a specific combination of an organic acid, an anionic surfactant, and a nonionic surfactant. In such embodiments, the organic acid may be glycolic acid, the anionic surfactant may be an alkyl sulfonate or an alkyl sulfate, and the nonionic surfactant may be an alcohol ethoxylate. In one or more embodiments, the antimicrobial activity of the compositions of the present invention may be due to the presence of glycolic acid, sodium octane sulfonate or sodium lauryl sulfate, and an alcohol ethoxylate, such as Neodol® 91-8.

In one or more embodiments, the antimicrobial activity of the compositions of the present invention may be due to the presence of a specific combination of an organic acid, an anionic surfactant, and an additional surfactant selected from anionic and nonionic surfactants. In such embodiments, the organic acid may be glycolic acid, the anionic surfactant may be sodium octane sulfonate and/or sodium lauryl sulfate, and the additional surfactant may be an alkyl sulfonate and/or an alcohol ethoxylate. In certain embodiments, the antimicrobial activity of the compositions of the present invention may be due to the presence of: 1) glycolic acid; 2) sodium octane sulfonate or sodium lauryl sulfate; and 3) an alcohol ethoxylate and/or an alpha-olefin sulfonate.

In various embodiments, the organic acid may be present in an amount of at least about 0.05, 0.1, 0.5, 1, 1.5, 2, 2.5, 3, 3.5, 4, 4.5, 5, 5.5, 6, 7, 8, 9, or 10 wt. %. In the same or alternative embodiments, the organic acid may be present in an amount of not more than about 30, 20, 15, 10, 9.5, 9, 8.5, 8, 7.5, 7, 6.5, 6, 5.5, 5, 4.5, or 4 wt. %. For example, in one or more embodiments, the organic acid may be present in an amount of from 0.05 to 30 wt. %, 0.1 to 20 wt. %, 0.5 to 15 wt. %, 1 to 10 wt. %, or 1.5 to 7.5 wt. %.

In various embodiments, one or more anionic surfactants (e.g., SOS, SLS and/or alpha-olefin sulfonate) may each be present in an amount of at least about 0.01, 0.05, 0.1, 0.2, 0.5, 1, 1.5, 2, 2.5, 3, 3.5, 4, 4.5, 5, 6, 7, 8, 9, or 10 wt. %. In the same or alternative embodiments, one or more anionic surfactants may be present in an amount of not more than about 35, 30, 20, 15, 10, 9.5, 9, 8.5, 8, 7.5, 7, 6.5, 6, 5.5, 5, 4.5, 4, 3.5, 3, 2.5, or 2 wt. %. For example, in certain embodiments, one or more anionic surfactants may each be present in an amount of from 0.01 to 35 wt. %, 0.05 to 30 wt. %, 0.1 to 20 wt. %, 0.5 to 15 wt. %, 1 to 10 wt. %, or 1.5 to 7.5 wt. %.

In certain embodiments, the compositions of the present invention comprise two or more anionic surfactants. In particular embodiments, the anionic surfactants are selected from the group consisting of SOS, SLS and alpha-olefin sulfonate. In particularly preferred embodiments, the anionic surfactants comprise alpha-olefin sulfonate and one of SOS and SLS. In these embodiments the weight ratio between the alpha-olefin sulfonate and the SOS or SLS present within the composition may be from 0.025:1 to 1:0.25, from 0.05:1 to 1:1, or from 0.15:1 to 1:2.

In various embodiments, the nonionic surfactant may be present in an amount of at least about 0.001, 0.005, 0.01, 0.05, 0.1, 0.2, 0.3, 0.4, 0.5, 1, 2, or 5%. In the same or alternative embodiments, the nonionic surfactant may be present in an amount of not more than about 25, 20, 15, 10, 7.5, 6.5, 5.5, 5, 4.5, 4, 3.5, 3, 2.5, 2, 1.5, 1, 0.5, 0.4, or 0.3 wt. %. For example in one or more embodiments, the nonionic surfactant may be present in an amount of from 0.001 to 25 wt. %, 0.005 to 20 wt. %, 0.01 to 15 wt. %, 0.05 to 10 wt. %, 0.1 to 5 wt. %, or 0.5 to 3.5 wt. %.

In certain embodiments, the total concentration of anionic and nonionic surfactants is at least about 0.05, 0.1, 0.5, 0.75, 1, 1.25, 1.5, 1.75, or 2 wt. %. In the same or alternative embodiments, the total concentration of anionic and nonionic surfactants is not more than about 40, 35, 30, 25, 20, 15, 10, 7.5, 5, 3, or 2.5 wt. %. For example, in one or more embodiments, the total concentration of anionic and nonionic surfactants is from 0.05 to 25 wt. %, 0.1 to 10 wt. %, 0.5 to 5 wt. %, or 0.75 to 2.5 wt. %.

In one or more embodiments, the compositions of the present invention comprise at least two anionic surfactants and a nonionic surfactant. One of the anionic surfactants is generally present in greater amounts than the other anionic surfactant. For example, one anionic surfactant may be present at a level that is at least 1.5 times, 2 times, 2.5 time, 3 times, 3.5 times, 4 times, 4.5 times, or 5 times greater than the other anionic surfactant. In particular embodiments, the majority anionic surfactant is SOS or SLS and the minority surfactant is alpha-olefin sulfonate. As discussed below, in certain embodiments it is desirable for the compositions of the present invention to non-irritating when applied to human or animal skin. Thus, it may be desirable to minimize the use of surfactants that are capable of causing skin irritation when used above certain levels. The nonionic surfactant may be present within the compositions at levels more even with the minority anionic surfactant. In such embodiments, the weight ratio of the minority anionic surfactant to the nonionic surfactant may be from 4:1 to 1:4, from 3:1 to 1:3, from 2:1 to 1:2, from 1.5:1 to 1 to 1:1.5, or from 1.25:1 to 1:1.25. In particular embodiments, the weight ratio between the majority anionic surfactant to the nonionic surfactant may be from 10:1 to 1:1, from 7.5:1 to 1.5:1, from 6:1 to 2:1, or from 5:1 to 2.5:1. In particular embodiments, the weight ratio between the organic acid and the total anionic and nonionic surfactant concentration is from 12:1 to 1:2, from 8:1 to 1:1.5, from 5:1 to 1:1, or from 3:1 to 1.5:1.

In one or more embodiments, a solvent may be present in the antimicrobial compositions of the present invention in an amount ranging from at least 50, 60, 70, or 75 wt. %, and/or not more than 99, 97, 95, or 90 wt. %. For example, in certain embodiments, a solvent may be present in amount ranging from 50 to 99 wt. %, 60 to 97 wt. %, 70 to 95 wt. %, or 75 to 90 wt. %. A non-limiting list of solvents includes water, an alcohol, propylene glycol, glycol ethers and/or alcohols. In certain embodiments, a mixture of two or more of the aforementioned solvents may be used.

The antimicrobial compositions of the present invention may include one or more additives, such as a buffering agent, an emollient, a humectant, a preservative, a barrier forming agent, a surfactant or wetting agent, a foaming agent, a viscosity control agent, a colorant, an opacifying agent, a skin conditioning agent, and an additional antimicrobial agent.

Barrier and film forming agents can be used in compositions formulated as teat dips so that the composition remains in contact with the teat between milking cycles. Barrier and film forming agents coat the teat skin and, optionally, the udder. Barrier agents may form a plug at the end of the open teat canal. Typical barrier and film forming agents include thick creams or emollients (made with viscosity control agents), films, polymers, latex and the like. Some nonionic surfactants may help further enhance the barrier properties of a composition, in addition to contributing to surface wetting. Examples of such surfactants may include, without limitation, polyoxyethylene-polyoxypropylene glycol (marketed as Pluronic® F108). Another commonly used barrier agent is marketed as Pluronic® P105. A latex material that provides an effective covering of the teat is described in U.S. Pat. No. 4,113,854, hereby incorporated by reference. Suitable barrier forming agents include, for example, latex, arabinoxylanes, glucomannanes, guar gum, johannistree gums, cellulose, methyl cellulose, ethyl cellulose, hydroxyethyl cellulose, hydroxymethyl cellulose, carboxyethyl cellulose, carboxymethyl cellulose, starch, hydroxyethyl starch, gum arabic, curdlan, pullulan, dextran, maltodextran, polysulfonic acid, polyacryl amide, high molecular weight polyacrylate, high molecular weight cross-linked polyacrylate, carbomer, sodium alginate, sodium alginate crosslinked with calcium salt, xanthan gum, poly(vinyl alcohol) (PVA) and poly(N-vinylpyrrolidone) (PVP). Preferred embodiments for barrier-forming agents include xanthan gum, carboxymethyl cellulose, sodium alginate, sodium alginate cross-linked with calcium salt, PVA, hydroxyethyl cellulose, PVP, and (2,5-dioxo-4-imidazolidinyl)-urea (Allantoin).

In certain embodiments, the compositions of the present invention may include a modified polysaccharide as a barrier film-forming agent to form a long-lasting persistent, continuous, uniform barrier film when applied to the skin. Such compositions have particular utility as barrier teat dips that are used prophylactically against mastitis. Such compositions may include relatively low molecular weight polysaccharides, for example, as may be derived specifically from hydrolyzed starch. Such compositions that are capable of forming a long-lasting, persistent, continuous, uniform barrier film may contain from about 0.1% to about 20% by weight of modified or hydrolyzed polysaccharide material for use as the barrier forming agent. The polysaccharide material may have a majority polysaccharide component as starch, modified starch, hydrolyzed starch, a starch derivative, and combinations thereof. In certain embodiments, the majority polysaccharide components may have overall or average Dextrose Equivalent (DE) value ranging from 2 to 50, and this value more preferably ranges from 3 to 27. In this sense, the term "majority polysaccharide component" is used to describe a majority weight percentage of all polysaccharides in the composition, i.e., more than 50% of all polysaccharides in the composition.

In certain embodiments, a foaming agent may be used in the disclosed antimicrobial compositions. A foaming agent aerates a liquid composition to produce a foam that may increase surface area of the composition and improve contact with the surface to be treated (e.g., an animal hoof or a teat). Typically, a foaming agent is in the form of a compressed gas, or a material that will decompose to release gas under certain conditions. Suitable gases include but are not limited to nitrogen, argon, air, carbon dioxide, helium and mixtures thereof. In addition, solid carbon dioxide (dry ice), liquid nitrogen, hydrogen peroxide and other substances that release gas via a change in state or through decomposition are contemplated for use with the present compositions. Typically, a high foaming surfactant, such as sodium lauryl sulfate, dodecylbenzene sulfonic acid, sodium alkylaryl polyether sulfate, sodium lauryl ether sulfate, sodium decyl sulfate, cocamine oxide, or $C_{12}$-$C_{14}$ whole coconut amido betaines, can be used to generate a stable foam. The foam may be produced when agitation in the form of a compressed gas is mixed with the solution either by bubbling the gas into the solution or spraying the solution or solution-gas mixture through spray equipment. In certain embodiments, foam may also be generated by the mechanical action, or by other mechanical means that mix atmospheric air with the composition.

Surfactants are well known for foaming and are widely used as foaming agents in hand soap and manual/hand dishwashing detergents, and may also be used as foaming agents in applications where foaming boosts the performance and increases the contact time of the composition to particular substrates. Examples of such suitable anionic surfactants can be chosen from a linear alkyl benzene sulfonic acid, a linear alkyl benzene sulfonate, an alkyl α-sulfomethyl ester, an α-olefin sulfonate, an alcohol ether sulfate, an alkyl sulfate, an alkylsulfo succinate, a dialkylsulfo succinate, and alkali metal, alkaline earth metal, amine and ammonium salts thereof. Specific examples are linear $C_{10}$-$C_{16}$ alkyl benzene sulfonic acid, linear $C_{10}$-$C_{16}$ alkyl benzene sulfonate or alkali metal, alkaline earth metal, amine and ammonium salts thereof, e.g., sodium dodecylbenzene sulfonate, sodium $C_{14}$-$C_{16}$ α-olefin sulfonate, sodium methyl α-sulfomethyl ester and disodium methyl α-sulfo fatty acid salts. Suitable nonionic surfactants may be chosen from an alkyl polyglucoside, an alkyl ethoxylated alcohol, an alkyl propoxylated alcohol, an ethoxylated-propoxylated alcohol, sorbitan, sorbitan ester, and an alkanol amide. Specific examples include $C_8$-$C_{16}$ alkyl polyglucoside with a degree of polymerization ranging from 1 to 3 e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{16}$ alkyl polyglucoside with a degree of polymerization of 1.6 (Glucopon® 625). Amphoteric surfactants can be chosen from alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate. Alkyl amine oxides based on $C_{12}$-$C_{14}$ alkyl chain length feedstock such as those derived from coconut oil, palm kernel oil may also be suitable foaming agents.

In one or more embodiments, viscosity control agents may be added to formulate the antimicrobial compositions according to an intended environment of use. In one example, it may be advantageous for some compositions to have an optimized solution viscosity to impart vertical clinging of the product onto a teat. This type of viscous product, especially one having a suitable thixotropic, pseudoplastic or viscoelastic gel strength, minimizes dripping of the product to avoid wastage and is particularly advantageous in teat dip compositions. Teat dip compositions may benefit from a preferred dynamic viscosity ranging from 1 cPs to 3000 cPs. Other applications including hard surface disinfectants have a preferred dynamic viscosity ranging from about 1 cPs to 300 cPs. In another example, the amount of viscosity control agents may be substantially reduced or even eliminated in other compositions, such as surface or floor disinfectants where easy cleanup is desired. An intermediate or medium viscosity composition may be useful in a hand cleaner or personal care product. It is within the scope of the present invention for the antimicrobial compositions to be formulated for a wide variety of applications by altering the amount of viscosity control agents. The viscosity referred to throughout this application is Brookfield viscosity measured in cPs by a Brookfield LV viscometer at ambient temperature (25° C.) with either spindle #1 @60-100 rpm or spindle #2 @15 to 30 rpm. In various embodiments, a thickener may be added to achieve a viscosity range of from 50 cPs to 10000 cPs, or from 100 cPs to 4000 cPs.

Suitable viscosity control agents include hemicellulose, for example arabinoxylanes and glucomannanes; plant gum materials, for example guar gum and johannistree gums; cellulose and derivatives thereof, for example methyl cellulose, ethyl cellulose, hydroxypropyl cellulose, hydroxyethyl cellulose or carboxymethyl cellulose; starch and starch derivatives, for example hydroxyethyl starch or cross linked starch; microbial polysaccharides, for example xanthan gum, sea weed polysaccharides, for example sodium alginate, carrageenan, curdlan, pullulan or dextran, dextran sulfate, whey, gelatin, chitosan, chitosan derivatives, polysulfonic acids and their salts, polyacrylamide, and glycerol. Preferred viscosity controlling agents are xantham gum, different types of cellulose and derivatives thereof, particularly hydroxyalkyl cellulose, methyl cellulose, and glycerol. In addition, high molecular weight (MW>1,000,000) cross-linked polyacrylic acid type thickening agents may be used, such as those sold by B.F. Goodrich (now Lubrizol) under their Carbopol® trademark, especially Carbopol® 941, which is the most ion-insensitive of this class of polymers, Carbopol® 940, and Carbopol® 934. The Carbopol® resins, also known as "Carbomer", are reported in U.S. Pat. No. 5,225,096 (hereby incorporated by reference into the present application), and are hydrophilic high molecular weight, cross-linked acrylic acid polymers. Carbopol® 941 has a molecular weight of about 1,250,000, Carbopol@940 has a molecular weight of approximately 4,000,000, and Carbopol® 934 has a molecular weight of approximately 3,000,000. The Carbopol® resins are cross-linked with polyalkenyl polyether, e.g. about 1% of a polyallyl ether of sucrose having an average of about 5.8 alkyl groups for each molecule of sucrose. Further detailed information on the Carbopol® resins is available from B.F. Goodrich (Lubrizol), see for example, the B. F. Goodrich catalog GC-67, Carbopol® Water Soluble Resins. Clays and modified clays such as bentonite or laponite can also be used as thickeners. Co-thickeners may be added to improve the stability of the gel matrix, for example, colloidal alumina or silica, fatty acids or their salts may improve gel stability. Further, the viscosity control agent may include carboxymethyl cellulose, sodium alginate, sodium alginate cross-linked with calcium salt, polysulfonic acids and their salts, polyacrylamide, polyvinyl alcohol (PVA), hydroxyethyl cellulose and polyN-vinylpyrrolidone) (PVP).

In one or more embodiments, a buffering agent, or a pH adjusting agent may be added to the disclosed compositions. A composition pH value may be selectively adjusted by the addition of acidic or basic ingredients. Generally, an acidic pH is preferred. Suitable acids for use as pH adjusting agents may include, for example, citric acid, formic acid, acetic acid, lactic acid, phosphoric acid, phosphorous acid, sulfamic acid, nitric acid, nitrous acid and hydrochloric acid. It will be recognized by those skilled in the art that the organic acid, e.g., glycolic acid, selected as the antimicrobial organic acid will also influence pH, and thus, have an adjusting effect as discussed in this paragraph. Mineral acids may be used to drastically lower the pH. The pH may be raised or made more alkaline by addition of an alkaline agent such as sodium hydroxide, potassium hydroxide, sodium carbonate, sodium bicarbonate, monosodium acid diphosphonate or combinations thereof. Traditional acid buffering agents such as citric acid, lactic acid, and phosphoric acid may also be used to maintain a desired pH. The pH value of the composition may be adjusted by the addition of acidic or basic or buffering materials.

The physical property of pH may be adjusted by acid or base addition, and is broadly preferred in the range of from about 2.0 to about 8.0 for use in teat dip compositions and other compositions that are intended to contact the skin. More preferred ranges include about 2.0 to about 7.5, about 2.2 to about 6.0, and about 2.5 to about 4.5. Hard surface and commercial disinfectants may be provided with lower pH values, such as about 2.0 or about 1.0.

As discussed above, in certain embodiments, the inventive compositions may include a wetting agent. Wetting agents or surface active agents are also known as surfactants. Typical wetting agents are used to wet the surface of application, reduce surface tension of the surface of application so that the product can penetrate easily on the surface and remove unwanted soil. The wetting agents or surfactants of the disclosed compositions may increase overall detergency of the formula, solubilize or emulsify some of the organic ingredients that otherwise would not dissolve or emulsify, and facilitate penetration of active ingredients deep onto the surface of the intended application surfaces, such as teat skin.

Suitable surfactants used as wetting agents in the present invention include anionic, cationic, nonionic, zwitterionic, and amphoteric surfactants. Wetting agents and surfactants used in the inventive applications can be high foaming, low foaming, and non-foaming type. Suitable anionic surfactants can be chosen from a linear alkyl benzene sulfonic acid, a linear alkyl benzene sulfonate, an alkyl a-sulfomethyl ester, an α-olefin sulfonate, an alcohol ether sulfate, an alkyl sulfate, an alkylsulfo succinate, a dialkylsulfo succinate, and alkali metal, alkaline earth metal, amine, and ammonium salts thereof. Specific examples include a linear $C_{10}$-$C_{16}$ alkyl benzene sulfonic acid or alkali metal, alkaline earth metal, amine, and ammonium salts thereof, e.g., sodium dodecylbenzene sulfonate; sodium $C_{14}$-$C_{16}$ α-olefin sulfonate; sodium methyl α-sulfomethyl ester; and disodium methyl α-sulfo fatty acid salt. Suitable nonionic surfactants can be chosen from an alkyl polyglucoside, an alkyl ethoxylated alcohol, an alkyl propoxylated alcohol, an ethoxylatedpropoxylated alcohol, sorbitan, sorbitan ester, an alkanol amide. Specific examples include $C_8$-$C_{16}$ alkyl polyglucoside with a degree of polymerization ranging from 1 to 3, e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{16}$ alkyl polyglucoside with a degree of polymerization of 1.6 (Glucopon® 625), and polyethoxylated polyoxypropylene block copolymers (poloxamers) including by way of example the Pluronic® poloxamers commercialized by BASF Chemical Co. Amphoteric surfactants can be chosen from alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate.

It will be recognizable to those skilled in the art that because at least one anionic surfactant and at least one nonionic surfactant are included as synergistic antimicrobial agents in the antimicrobial compositions of the present invention, these surfactants may also have an influence on the wetting properties of the mixture.

An opacifying agent or dye may be optionally included in the present compositions. For example, color on a teat tells a farmer that a particular cow has been treated. To preclude any problems with possible contamination of milk, it is preferred that FD&C Certified (food grade) dyes be used. There are many FD&C dyes available, such as FD&C Red #40, FD&C Yellow #6, FD&C Yellow #5, FD&C Green #3, and FD&C Blue #1. Dyes used either alone or in combination are preferred. D&C Orange #4 can also be used. Titanium dioxide ($TiO_2$) is widely used as an opacifier and can also be used in combination with various colorants.

In certain embodiments, a preservative may be included in the inventive compositions. A non-limiting list of preservatives includes ethylenediaminetetraacetic acid (EDTA) and its alkali salts, paraban, methyl paraban, ethyl paraban, glutaraldehyde, benzyl alcohol, and low molecular weight alcohols having a carbon number less than five. In one or more embodiments, more than one type of preservative may be utilized. It is known to one skilled in the art that chelating agents, such as EDTA, function as preservatives by sequestering or removing metal ions from hard water. The metal ions, if not removed from the composition, serve as reaction sites for enzymes within the bacteria; the metalloenzyme reactions produce energy for bacterial cell replication.

In certain embodiments, one or more skin conditioning agents may be included in the inventive compositions. Skin conditioning agents may provide extra protection for human or animal skin prior to or subsequent to being exposed to adverse conditions. For example, skin conditioning agents may include moisturizers, such as glycerin, sorbitol, propylene glycol, D-Panthenol, Poly Ethylene Glycol (PEG) 200-10,000, Poly Ethylene Glycol Esters, Acyl Lactylates, Polyquaternium-7, Glycerol Cocoate/Laurate, PEG-7 Glycerol Cocoate, Stearic Acid, Hydrolyzed Silk Peptide, Silk Protein, Aloe Vera Gel, Guar Hydroxypropyltrimonium Chloride, Alkyl Poly Glucoside/Glyceryl Luarate, shea butter and coco butter; sunscreen agents, such as titanium dioxide, zinc oxide, octyl methoxycinnamate (OMC), 4-methylbenzylidene camphor (4-MBC), oxybenzone and homosalate; and itch-relief or numbing agents, such as aloe vera, calamine, mint, menthol, camphor, antihistamines, corticosteroids, benzocaine and paroxamine HCl.

As shown in the Examples below, the antimicrobial compositions of the present invention that include an organic acid, an anionic surfactant, and an nonionic surfactant, exhibit antimicrobial activity in the absence of other antimicrobial agents. In one or more embodiments, however, it may be advantageous to include in the disclosed compositions an additional antimicrobial agent, e.g., a traditional antimicrobial agent. For example, in certain embodiments, the antimicrobial compositions of the present invention may be used in combination with traditional antimicrobial agents to achieve effective kill rates at lower concentrations of traditional antimicrobial agents than those typically used when the traditional antimicrobial agents provide the sole source of antimicrobial activity.

Traditional antimicrobial agents include iodophors, quaternary ammonium compounds, hypochlorite releasing compounds (e.g. alkali hypochlorite, hypochlorous acid), oxidizing compounds (e.g. peracids and hypochlorite), protonated carboxylic acids (e.g. heptanoic, octanoic, nonanoic, decanoic, undecanoic acids), acid anionics (e.g. alkylaryl sulfonic acids, aryl sulfonic acid, alkyl sulfonic acids, alkylaryl sulfuric acid, aryl sulfuric acid, alkyl sulfuric acid, alkylaryl sulfuric acid), chlorine dioxide from alkali chlorite by an acid activator, and bisbiguanides such as chlorhexidine. Phenolic antimicrobial agents may be chosen from 2,4,4'-trichloro-2"-hydroxydiphenylether, which is known commercially as triclosan and may be purchased from Ciba Specialty Chemicals as IRGASAN™ and IRGASAN DP 300™. Another such antimicrobial agent is 4-chloro-3,5-dimethyl phenol, which is also known as PCMX and is commercially available as NIPACIDE PX and NIPACIDE PX-P. Other traditional germicides include formaldehyde releasing compounds such as glutaraldehyde and 2-bromo-2-nitro-1,3-propanediol (Bronopol), polyhexamethyl biguanide (CAS 32289-58-0), guanidine salts such as polyhexamethylene guanidine hydrochloride (CAS 57028-96-3), polyhexamethylene guanidine hydrophosphate (89697-78-9), and poly[2-(2-ethoxy)-ethoxyethyl]-guanidinium chloride (CAS 374572-91-5) and mixtures thereof.

In one embodiment, the disclosed antimicrobial compositions may be used in combination with traditional antimicrobial agents, such as copper sulfate, zinc sulfate, sulfamethazine, quaternary ammonium compounds, hydrogen peroxide and/or peracetic acid, for example, to achieve an effective kill at lower concentrations of traditional antimicrobial agents.

In one or more embodiments, the antimicrobial compositions of the present invention do not include hydrogen peroxide (or hydrogen peroxide generating compounds), chlorine dioxide (or chlorine dioxide generating compounds), chlorhexidine, iodophors, and/or iodine. In one or more embodiments, the antimicrobial compositions of the present invention are iodine free. In certain embodiments, the antimicrobial compositions of the present invention are hydrogen peroxide free. In one or more embodiments, the antimicrobial compositions of the present invention are chlorhexidine free. In certain embodiments, the antimicrobial compositions of the present invention are chlorine dioxide free.

The antimicrobial compositions of the present invention may provide a substantial reduction in Gram positive and Gram negative bacteria, as well other numerous classes of microbes. In particular embodiments, the reduction may be at least about a three, four, five, or six log reduction in Gram positive and/or Gram negative bacteria. In certain embodiments, the antimicrobial compositions may exhibit a substantially complete kill that is at least a five log (99.999%) reduction in bacterial populations. In embodiments, the antimicrobial compositions may provide any of the foregoing log reductions within one minute, 45 seconds, 30 seconds, or 15 seconds of contact time when tested according to EN 1656, at 25° C., as described in the Examples below.

In certain embodiments, the antimicrobial compositions may be used for prophylactic treatment of a dairy animal's teats to provide a long lasting persistent protective germicidal barrier film that demonstrates persistence between milkings, and is controllably reproducible to yield a continuous, uniform persistent barrier. This treatment process may include milking the animal, coating the teats with the composition after milking, allowing the composition to dry and so also form a layer of persistent barrier film on the teats. In certain other embodiments, the compositions of the present invention may be used as a germicide on an animal's teats but may not form a long lasting persistent barrier film on the teats. In various embodiments, the composition may be applied topically by painting, foaming, dipping or spraying. Furthermore, use of the composition is not limited to use against mastitis, and the composition may be used generally to treat or protect against any infectious skin condition.

In certain other embodiments, the antimicrobial compositions of the present invention may be used, for example, in any manner where application of antimicrobial agents is desired. In one or more embodiments, the antimicrobial compositions of the present invention may be used as a hand sanitizer, a skin cleanser, a surgical scrub, a wound care agent, a disinfectant, a mouthwash, a bath/shower gel, a hard surface sanitizer and the like. Preferred compositions for skin applications have a pH of about 2.0 to about 8.0 and provide a substantial reduction, e.g., greater than a five log reduction (99.999%), in Gram positive and Gram negative bacterial populations. In certain embodiments, the antimicrobial compositions of the present invention may be applied as a wound healing agent, where the composition assists in a faster and qualitatively improved healing of wounds by decreasing the number of microorganisms in the vicinity of the wound.

In one or more embodiments, the antimicrobial compositions of the present invention may be non-irritating when topically applied to animal or human skin. A composition may be determined to be non-irritating based on its Lysis/Denaturation (L/D) ratio as determined by Blood Cell Irritation testing.

The Blood Cell Irritation tests measures the L/D ratio of a particular composition and is used to determine if a particular composition is mild enough for topical application to the skin or human or animal. Measuring the L/D ratio requires measuring the half haemolysis value (H50) and the denaturation index (DI). The H50 value relates to the tendency of the red blood cells to rupture when in contact with the test product. The DI value relates to the denaturation of protein caused by the test product.

Haemolysis Values (H50); Product Denaturation Index Values (DI); and Lysis/Denaturation Ratios (L/D) can be determined for the compositions using known methods. Descriptions of these methods are disclosed by Wolfgang J. W. Pape, Udo Hoppe: *In vitro Methods for the Assessment of Primary Local Effects of Topically Applied Preparations*, Skin Pharmacol. (1991), 4, 205-212, which is incorporated herein by reference.

These methods involve separating red blood cells and then exposing them to the test compositions. To separate the red blood cells, 50 mL of sodium citrate buffer (17.03 g trisodium citrate+8.45 g citric acid diluted to 1 L with bacteria-free DI water) is added to every 450 mL of fresh calf blood and mixed. The blood is then centrifuged to isolate the red blood cells (RBC), which are then washed with phosphate buffered saline solution (PBS) (3.15 g of $Na_2HPO_4$+0.762 g of $KH_2PO_4$+7.21 g of NaCl+1.8 g of glucose diluted to 1 L with bacteria-free DI water), and centrifuged several times to remove white cells and plasma, according to a known method. The red blood cells ("RBC stock") are then placed into containers for use in testing the compositions of interest.

Further, a Standard Surfactant Solution is prepared that includes 1000 ppm sodium lauryl sulfate in PBS. Also, this Standard Surfactant Solution is diluted to 0 ppm, 20 ppm, 30 ppm, and 40 ppm. A Test Product Solution is also prepared, which includes 1000 ppm test product in PBS. In addition, this Test Product is diluted to 0 ppm, 25 ppm, 50 ppm, and 100 ppm.

To measure the H50 value of a test formulation, the H50 value of the Standard Surfactant Solution is first measured. 0.25 mL of adjusted RBC stock suspension is mixed with 9.75 mL of the 40 ppm Standard Surfactant Solution. The mixture is then shaken for 10 minutes and centrifuged for 3 minutes at 5000 rpm to precipitate any intact RBC. The absorbance at 560 nm is measured using the 0 ppm test Standard Surfactant Solution as a blank. This procedure is then repeated for the 20 ppm and 30 ppm Standard Surfactant Solutions. A graph of concentration in ppm vs. absorbance at 560 nm is plotted for the Standard Surfactant Solution. The H50 concentration is the concentration where the absorbance is equal to half the absorbance of the 100% haemolysis value (H100), which is determined by mixing 0.25 mL of adjusted RBC Stock with 9.75 mL of DI water, then shaking the mixture for 10 minutes, and then measuring the absorbance at 560 nm. The half-maximal haemolytic concentration of sodium lauryl sulfate is 22+4 ppm. Obtaining a value in this range confirms that the proper procedure is being followed.

The H50 value of the Test Product is then measured. 0.25 mL of adjusted RBC Stock suspension is mixed with 9.75 mL of one of the Test Product solutions. The mixture is then shaken for 10 minutes and centrifuged for 3 minutes at 5000 rpm to precipitate any intact RBC. The absorbance at 560 nm is measured using the 0 ppm Test Product sample as a blank. These steps are repeated for each concentration of Test Product solutions. A graph of concentration in ppm vs. absorbance at 560 nm for the Test Product is then plotted. The H50 concentration is the concentration where the absorbance is equal to half the absorbance of the H100. If necessary, additional concentrations of the test product can be prepared so the H50 can be measured accurately.

To determine the DI value, the Standard Surfactant Denaturation Index R2 value is measured. 0.25 mL of adjusted RBC Stock suspension is mixed with 9.75 mL of the 1000 ppm Standard Surfactant Solution. The mixture is then shaken for 10 minutes and centrifuged for 3 minutes at 5000 rpm to precipitate any intact RBC. All of the RBC should dissolve. The absorbance at 575 nm and 540 nm is measured using the 0 ppm Standard Surfactant Solution as a blank. The ratio of ABS575/ABS540 is equal to R2. R2 is approximately equal to 0.8. Obtaining a value in this range confirms that the proper procedure is being followed.

The DI value of the Test Product is determined by first mixing 0.25 mL of adjusted RBC Stock suspension with 9.75 mL of the 1000 ppm Test Product solution. The mixture is then shaken for 10 minutes and centrifuged for 3 minutes at 5000 rpm to precipitate any intact RBC. All of the RBC should dissolve. If the RBC are not completely dissolved, repeat with a higher concentration of Test Product. The absorbance at 575 nm and 540 nm is measured using the 0 ppm Test Product solution as a blank. The ratio of ABS575/ABS540 is equal to $R_i$. The Ri and R2 values are then used to calculate the DI from formula 1 below.

$$DI(\%)=100(1.05-R_i)/(1.05-R2) \qquad \text{Formula 1}$$

The H50 score, which measures haemolysis alone, usually shows a similar irritation correlation to the L/D ratio. The higher the ppm value for H50 the less irritating the product. A crude scale is H50>500 ppm (non-irritant); 120-500 (slight irritant), 30-120 (moderate irritant), 10-30 (irritant), 0-10 (strong irritant). In certain embodiments, the antimicrobial compositions of the present invention may exhibit an H50 value of at least 300, 400, 500, 600, 700, or 800 ppm.

The DI score, which measures denaturation of protein also shows a correlation to the L/D ratio. A crude scale is DI 0-5% (non-irritant); 5-10% (slight irritant), 10-75% (moderate irritant), 75-100% (irritant), and >100% (strong irritant). In certain embodiments, the antimicrobial compositions of the present invention may exhibit a DI score of less than about 10, 7, 5, 3, 1, 0.5, or 0.3%.

However, as discussed above, the L/D ratio is the primary value typically used to determine irritation. An L/D value greater than 100 is an indication that the composition is a non-irritant; levels between 10 and 100 are considered slight irritants; levels between 1 and 10 are considered moderate irritants; levels between 0.1 to 1 are considered irritants; and levels lower than 0.1 are considered strong irritants. In certain embodiments, the antimicrobial compositions of the present invention exhibit an L/D ratio of at least 100, 150, 200, 250, or 300. In certain embodiments, because the combination of an organic acid, an anionic surfactant, and a nonionic surfactant may not be a skin irritant, skin conditioning and moisturizing agents are at best unnecessary, and at least may be minimized in a particular product.

Methods of preparing the antimicrobial compositions of the present invention may involve dissolving a desired concentration of antimicrobial agents and, optionally, any desired additives in a selected solvent. The solution is then mixed, for example in a mixer, to form a final antimicrobial composition.

In certain embodiments, the components of the disclosed antimicrobial compositions fall within the ranges set forth in Tables I(a)-I(c) below. It should be understood that the concentration ranges listed for each broad component category in Tables I(a)-I(c), in certain embodiments, may apply to each component within that broad category. For example, with reference to the most preferred concentration ranges listed in Table I(a), if two anionic surfactants are present in a particular embodiment, than each anionic surfactant may be present in an amount of from 0.1-30 wt. %.

TABLE I(a)

Ranges of Components (% w/w) of the Antimicrobial Compositions

| | Broadly Preferred | Preferred | Most Preferred |
|---|---|---|---|
| Organic acid | 0.01-70 | 0.05-50 | 0.1-30 |
| Anionic surfactant | 0.01-70 | 0.05-50 | 0.1-30 |
| Nonionic surfactant | 0.01-70 | 0.05-50 | 0.1-30 |
| Additives | 0-50 | 0.1-35 | 0.5-25 |
| Water | 0.01-99.9 | 1-95.0 | 1.5-90 |
| pH adjusting agent | 0-20 | 0.05-15 | 0.1-10 |

It should be understood that the concentration ranges listed in Table I(a) above may apply to a ready-to-use (RTU) formulation or as a concentrate that requires dilution in a solvent prior to use. In certain embodiments, the disclosed antimicrobial compositions, when in the form of a concentrate, may be diluted by at least about 1/1, 1/2, 1/3, 1/5, 1/10, 1/25, 1/50, 1/100, 1/200, or 1/500 to form a RTU composition. In accordance with various other embodiments, Tables I(b) and I(c) disclose concentration ranges specific for RTU formulations and for concentrate formulations, respectively.

TABLE I(b)

Ranges of Components (% w/w) of the Antimicrobial Compositions in RTU Formulations

| | Broadly Preferred | Preferred | Most Preferred |
|---|---|---|---|
| Organic acid | 0.1-10 | 0.5-5 | 1.0-5.0 |
| Anionic surfactant | 0.1-10 | 0.5-5 | 1.0-3.0 |
| Nonionic surfactant | 0.01-10 | 0.05-5 | 0.1-3.0 |
| Additives | 0-50 | 0.1-35 | 0.5-25 |
| Water | 0.01-99.9 | 1-95.0 | 1.5-90 |
| pH adjusting agent | 0-20 | 0.05-15 | 0.1-10 |

TABLE I(c)

Ranges of Components (% w/w) of the Antimicrobial Compositions in Concentrate Form

| | Broadly Preferred | Preferred | Most Preferred |
|---|---|---|---|
| Organic acid | 0.2-80 | 1-50 | 2-30 |
| Anionic surfactant | 0.2-80 | 1-50 | 2-6 |
| Nonionic surfactant | 0.02-20 | 0.1-10 | 0.2-6.0 |
| Additives | 0-80 | 0.2-70 | 1-50 |

TABLE I(c)-continued

Ranges of Components (% w/w) of the Antimicrobial Compositions in Concentrate Form

| | Broadly Preferred | Preferred | Most Preferred |
|---|---|---|---|
| Water | 0.01-99.9 | 1-95.0 | 1.5-90 |
| pH adjusting agent | 0-20 | 0.05-15 | 0.1-10 |

Through experimentation, as shown in the Examples below, it has been discovered that an organic acid, in combination with an anionic surfactant and a nonionic surfactant provide a synergistic result enabling greater than a five-log reduction (99.999%) in both Gram-negative and Gram-positive bacteria, while still avoiding conventional oxidizers and other conventional antimicrobial agents, which can be harmful to the animal's skin.

EXAMPLES

This invention can be further illustrated by the following Examples of embodiments thereof, although it will be understood that these examples are included merely for the purposes of illustration and are not intended to limit the scope of the invention unless otherwise specifically indicated.

It should be recognized that in the below Examples, each component's concentration is 100% active unless that component is expressly identified as having a certain percentage of active versus inert ingredients. For example, if a component is listed as "Glycolic acid, 70%" and is shown to be present at 4.28 wt. %, this means that glycolic acid is present in that composition at 3 wt % (0.7*4.28 wt. %).

Example 1

Antimicrobial Activity of Formulations Having Varying Concentrations of Anionic and Nonionic Surfactants Various standardized test methods are in place for comparatively testing the efficacy of antimicrobial agents. The preferred standard is defined as AOAC Official Method 960.09, as published by the Association of Analytical Chemists (AOAC International) in 2000 (Association of Official Analytical Chemists. 1990 (Official Methods of Analysis, Pages 138-140 in Germicidal and Detergent Sanitizing Action of Disinfectants 960.09, Vol. I. 15th ed. AOAC, Arlington, Va.). Europeans tend to use other standards for this same purpose, such as the EN 1040, EN1656, and EN 14885 test methods. All of these standards are hereby incorporated by reference to the same extent as though fully disclosed herein. In the present Example, test method EN 1656 was utilized.

According to a modified EN1656 dilution neutralization method, freeze dried *E. coli* (ATCC 11229), *S. aureus* (ATCC 6538), *Streptococcus uberis, Pseudomonas aeruginosa, Streptococcus dysgalactiae*, and *Streptococcus agalactiae* were hydrated, grown for four days and transferred. Then the bacteria were diluted to form a suspension having an initial concentration of about $10^7$ cfu/mL.

Sterilized skimmed milk was used as an interfering substance in all testing instead of bovine albumin as in EN 1656 protocol. 1 mL of milk and 1 mL of bacterial suspension were mixed and left in contact for 2 minutes at 25° C. 8 mL of the formulations described below in Table II were then added to the mixture and left in contact for 15 seconds at 25° C. One milliliter of the resulting solution was removed and diluted with 9 mL of phosphate buffer at pH 7.2, and then four successive dilutions were made. Samples from each dilution were plated in duplicate and agar was added. One mL of the previous mixture was added to 9 mL of neutralizing solution and then mixed. Three serial dilutions were made of this solution and 1 mL of each solution was dispensed into a Petri dish in duplicate. Also, 0.1 mL of the most dilute solution was dispensed in duplicate. Approximately 15 mL of sterile tryptone glucose extract agar was added to each Petri dish and when solidified, each plate was incubated at 37° C. for 24 hours. This procedure was repeated for all samples to be tested.

For controls, the $10^7$ cfu/mL bacteria suspensions were diluted to concentrations of $10^4$ and $10^3$ cfu/mL. One milliliter of the $10^4$ cfu/mL dilutions and 0.1 mL of the $10^3$ cfu/mL dilutions (done in triplicate) were dispensed onto Petri dishes and approximately 15 mL of tryptone glucose extract agar was added. When solidified, the plates were incubated at 37° C. for 24 hours. An average of the plate counts for the triplicate platings of the $10^3$ cfu/mL dilution was considered the initial numbers control count.

The plates with bacterial populations between 25 and 250 were counted and results were expressed as logarithmic reductions according to EN 1656 test method. Table II below provides the results of the EN 1656 test and the formulations tested. Witconate AOS is a $C_{14}$-$C_{16}$ alpha-olefin sulfonate (sulfonic acids, $C_{14}$-$C_{16}$-alkane hydroxyl and $C_{14}$-$C_{16}$-alkene, sodium (CAS #68439-57-6)). The CAS# for the sodium octane sulfonate is 142-31-4, and the CAS# for Neodol® 91-8 is 68439-46-3. Table II also provides the results of irritation testing of Formulation B. The H50, DI, and L/D values for the irritation testing were determined as described above.

TABLE II

Formulations with Glycolic Acid and with and without Sodium Octane Sulfonate

| Ingredients and Concentration | Formulations | | | | | |
|---|---|---|---|---|---|---|
| (% w/w) | A | B | C | D | E | F |
| Water | 86.58 | 85.33 | 82.53 | 81.03 | 84.31 | 82.31 |
| Keltrol RL (Xanthan Gum) | 0.05 | 0.05 | 0.05 | 0.05 | 0.05 | 0.05 |
| Glycerin | 5.0 | 5.0 | 5.0 | 5.0 | 5.0 | 5.0 |
| Glycolic acid, 70% | 4.28 | 4.28 | 4.28 | 4.28 | 4.28 | 4.28 |
| Sodium Octane Sulfonate, 36% | 2.78 | 2.78 | 2.78 | 8.33 | 0 | 0 |
| Witconate AOS, 40% | 0 | 1.25 | 3.75 | 0 | 3.75 | 6.25 |
| Neodol 91-8 | 0.20 | 0.20 | 0.50 | 0.20 | 1.5 | 1.0 |
| FD&C #1 Blue | 0.008 | 0.008 | 0.008 | 0.008 | 0.008 | 0.008 |
| Sodium hydroxide, 50% | 1.10 | 1.10 | 1.10 | 1.10 | 1.10 | 1.10 |
| Micro Test: EN 1656, 15 second contact time@ 25° C.; Results are in log reduction from initial Bacteria Count $10^7$ cfu/mL | | | | | | |
| Staphyloccocus aureus | 4.43 | 6.25 | 6.25 | 6.25 | 6.25 | 6.25 |
| Escherichia coli | 4.95 | 6.29 | 6.29 | 6.29 | 2.10 | 2.03 |
| Strep uberis | 5.79 | 5.79 | 5.79 | 5.79 | 1.78 | 1.66 |
| Pseudomonas aeruginusa | 5.70 | 5.70 | 5.70 | 5.70 | 1.52 | 1.48 |
| Streptococcus dysgalactiae | 6.17 | 6.17 | 6.17 | 6.17 | 1.77 | 1.70 |
| Streptococcus agalactiae | 5.81 | 5.81 | 5.81 | 5.81 | 5.81 | 5.81 |
| Irritation Test: | | | | | | |
| H50 value (ppm) | X | 3000 | X | X | X | X |
| DI value (%) | X | 3.26 | X | X | X | X |
| L/D ratio | X | 920 | X | X | X | X |

X = not tested

The results from Table II demonstrate that compositions comprising glycolic acid, an alcohol ethoxylate, and sodium octane sulfonate can exhibit antimicrobial activity that causes over a 4 log reduction in several different types of bacteria. In addition, the results show that that antimicrobial efficacy is dependent upon the presence of the anionic surfactant sodium octane sulfonate. For example, Formulations A-D, which include sodium octane sulfonate, all exhibit at least a four log reduction in all types of bacteria tested, while Formulations E and F, which lack sodium octane sulfonate, exhibit significantly less antimicrobial activity, e.g., about a 2-log reduction, in several of the types of bacteria tested. Further, comparing Formulations A and D show that by increasing the concentration of sodium octane sulfonate, the level of antimicrobial activity increases to maximum efficacy, i.e., at least a 5 log reduction in all types of bacteria tested.

Example 2

Antimicrobial Activity of Formulations Having Varying Concentrations of Sodium Octane Sulfonate In this Example, varying concentrations of Sodium Octane Sulfonate were tested for antimicrobial efficacy. The formulations were subjected to the EN 1656 test as described above in Example 1. The results appear in Table III below.

TABLE III

Formulations with Glycolic Acid and Varying Concentrations of Sodium Octane Sulfonate

| Ingredients and Concentration | Formulations | | | | |
|---|---|---|---|---|---|
| (% w/w) | A | B | C | D | E |
| Water | 85.33 | 84.78 | 83.94 | 85.61 | 86.16 |
| Keltrol RL (Xanthan Gum) | 0.05 | 0.05 | 0.05 | 0.05 | 0.05 |
| Glycerin | 5.0 | 5.0 | 5.0 | 5.0 | 5.0 |
| Glycolic acid, 70% | 4.28 | 4.28 | 4.28 | 4.28 | 4.28 |
| Sodium Octane Sulfonate, 36% | 2.78 | 3.33 | 4.17 | 2.50 | 1.95 |
| Witconate AOS, 40% | 1.25 | 1.25 | 1.25 | 1.25 | 1.25 |
| Neodol 91-8 | 0.20 | 0.20 | 0.20 | 0.20 | 0.20 |
| FD&C #1 Blue | 0.008 | 0.008 | 0.008 | 0.008 | 0.008 |

TABLE III-continued

Formulations with Glycolic Acid and Varying Concentrations of Sodium Octane Sulfonate

| Ingredients and Concentration | Formulations | | | | |
|---|---|---|---|---|---|
| (% w/w) | A | B | C | D | E |
| Sodium hydroxide, 50% | 1.10 | 1.10 | 1.10 | 1.10 | 1.10 |
| Micro Test: EN 1656, 15 second contact time@ 25° C.; Results are in log reduction from initial Bacteria Count $10^7$ cfu/mL | | | | | |
| Staphyloccocus aureus | 6.28 | 6.28 | 6.28 | 5.86 | 5.39 |
| Escherichia coli | 6.39 | 6.39 | 6.39 | 6.73 | 6.73 |
| Strep uberis | 6.32 | 6.32 | 6.32 | X | X |
| Pseudomonas aeruginosa | 6.37 | 6.37 | 6.37 | X | X |
| Streptococcus dysgalactiae | 6.31 | 6.31 | 6.31 | X | X |
| Streptococcus agalactiae | 5.95 | 5.95 | 5.95 | X | X |

X = not tested

The results from Table III demonstrate that formulations having varying concentrations of sodium octane sulfonate (between 0.7 to 1.5 wt. %) exhibit maximum antimicrobial efficacy, i.e., at least a 5 log reduction in all types of bacteria tested.

Example 3

Antimicrobial Activity of Formulations Having Varying Concentrations of Sodium Lauryl Sulfate In this Example, formulations having varying concentrations of Sodium Lauryl Sulfate were tested for antimicrobial efficacy. The formulations were subjected to the EN 1656 test as described above in Example 1. The results appear in Table IV below. The CAS# of sodium lauryl sulfate is 151-21-3. Table IV also provides the results of irritation testing of Formulation A. The H50, DI, and L/D values for the irritation testing were determined as described above.

TABLE IV

Formulations with Glycolic Acid and Sodium Lauryl Sulfate

| Ingredients and Concentration | Formulations | | | | |
|---|---|---|---|---|---|
| (% w/w) | A* | B | C | D | E |
| Water | 86.03 | 79.36 | 84.78 | 81.98 | 85.49 |
| Keltrol RL (Xanthan Gum) | 0.05 | 0.05 | 0.05 | 0.05 | 0.05 |
| Glycerin | 5.0 | 5.0 | 5.0 | 5.0 | 5.0 |
| Glycolic acid, 70% | 4.28 | 4.28 | 4.28 | 4.28 | 4.29 |
| Sodium Lauryl Sulfate, 30% | 3.33 | 10.0 | 3.33 | 3.33 | 3.33 |
| Witconate AOS, 40% | 0 | 0 | 1.25 | 3.75 | 0.63 |
| Neodol 91-8 | 0.20 | 0.20 | 0.20 | 0.50 | 0.20 |
| FD&C #1 Blue | 0.008 | 0.008 | 0.008 | 0.008 | 0.008 |
| Sodium hydroxide, 50% | 1.10 | 1.10 | 1.10 | 1.10 | 1.0 |
| Micro Test: EN 1656, 15 second contact time@ 25° C.; Results are in log reduction from initial Bacteria Count $10^7$ cfu/mL | | | | | |
| Staphyloccocus aureus | 6.25 | 6.25 | 6.25 | 6.25 | 6.6 |
| Escherichia coli | 6.29 | 6.29 | 6.29 | 6.29 | 4.8 |
| Strep uberis | 5.79 | 5.79 | 5.79 | 5.79 | X |
| Pseudomonas aeruginosa | 5.70 | 5.70 | 5.70 | 5.70 | X |
| Streptococcus dysgalactiae | 6.17 | 6.17 | 6.17 | 6.17 | X |
| Streptococcus agalactiae | 5.81 | 5.81 | 5.81 | 5.81 | X |
| Irritation Test: | | | | | |
| Half-haemolysis (H50) value (ppm) | X | X | 1300 | X | X |
| Denaturation Index (DI) value (%) | X | X | 9.60 | X | X |
| L/D value | X | X | 135 | X | X |

X = not tested
*The germicidal results for this formulation were not in line with data generated for other formulations without AOS. Therefore, the germicidal efficacy for E. coli and S. aureus was retested. The log reductions for E. coli and S. aureus were 4.7 and 5.3, respectively. These results were in line with other data points.

The results from Table IV demonstrate that antimicrobial compositions comprising glycolic acid, an alcohol ethoxylate, AOS, and sodium lauryl sulfate can exhibit maximum antimicrobial efficacy, i.e., at least a 5 log reduction in all types of bacteria tested, provided that greater than 0.25 wt. % (absolute) of AOS was employed.

Example 4

Antimicrobial Activity of Formulations Having Glycolic Acid and Various Surfactants In this Example, formulations having glycolic acid and various anionic, cationic, and nonionic surfactants were tested for antimicrobial efficacy. The formulations were subjected to the EN 1656 test as described above in Example 1. The results appear in Table V below. Glucopon® 225 DK is the trade name for alkylpolyglycoside $C_8$-$C_{10}$ (CAS#68515-73-1). Sodium xylene sulfonate has a CAS # of 1300-72-7. Barlox® 12 is the trade name for N-Cocoalkyl-N,N-dimethylamine oxide (CAS #61788-90-7). Colalipid C is the trade name for Cocamidopropyl PG-Dimonium Choride Phosphate (CAS #83682-78-4).

TABLE V

Formulations with Glycolic Acid and Various Surfactants

| Ingredients and Concentration | Formulations | | | |
|---|---|---|---|---|
| (% w/w) | A | B | C | D |
| Water | 79.56 | 85.27 | 81.86 | 80.24 |
| Keltrol RL (Xanthan Gum) | 0.05 | 0.05 | 0.05 | 0 |
| Glycerin | 5.0 | 5.0 | 5.0 | 5.0 |
| Glycolic acid, 70% | 4.28 | 4.28 | 4.28 | 4.28 |
| Glucopon ® 225 DK, 70% | 0 | 4.29 | 0 | 0 |
| Sodium xylene sulfonate, 40% | 0 | 0 | 7.5 | 0 |

TABLE V-continued

Formulations with Glycolic Acid and Various Surfactants

| Ingredients and Concentration (% w/w) | Formulations | | | |
|---|---|---|---|---|
| | A | B | C | D |
| Barlox ® 12, 30% | 10.0 | 0 | 0 | 0 |
| Colalipid C, 45% | 0 | 0 | 0 | 6.67 |
| Witconate AOS, 40% | 0 | 0 | 0 | 2.5 |
| Neodol 91-8 | 0.0 | 0.0 | 0.2 | 0.2 |
| FD&C #1 Blue | 0.008 | 0.008 | 0.008 | 0.008 |
| Sodium hydroxide, 50% | 1.10 | 1.10 | 1.10 | 1.10 |
| Micro Test: EN 1656, 15 second contact time @ 25° C.; Results are in log reduction from initial Bacteria | | | | |
| Count 10⁷ cfu/mL | | | | |
| Staphyloccocus aureus | 1.0 | 0.53 | 1.00 | 2.27 |
| Escherichia coli | 6.16 | 4.93 | 3.09 | 0.74 |

The results from Table V show that maximum antimicrobial efficacy, i.e., at least a 5 log reduction in all types of bacteria tested, cannot be obtained in formulations having glycolic acid and the above tested nonionic, cationic, and anionic surfactants. These results, in combination with the results in Examples 1-3 and 5, demonstrate that glycolic acid cannot be combined with just any surfactants to exhibit maximum antimicrobial efficacy.

Example 5

Antimicrobial Activity of Formulations in the Presence and Absence of Glycolic Acid, Sodium Octane Sulfonate, and Sodium Lauryl Sulfate In this Example, a series of control experiments were conducted testing the effect that glycolic acid, sodium octane sulfonate, and sodium lauryl sulfate has on antimicrobial activity. Specifically, formulations were tested that included: increasing amounts of glycolic acid but no sodium octane sulfonate or sodium lauryl sulfate (Formulations A-E); no glycolic acid but sodium octane sulfonate or sodium lauryl sulfate (Formulations F and G); and a control formulation having glycolic acid and sodium octane sulfonate (Formulation H). The formulations were subjected to the EN 1656 test as described above in Example 1. The results appear in Table VI below.

TABLE VI

Formulations with and without Glycolic Acid, Sodium Octane Sulfonate, and Sodium Lauryl Sulfate

| Ingredients and Concentration (% w/w) | Formulations | | | | | | | |
|---|---|---|---|---|---|---|---|---|
| | A | B | C | D | E | F | G | H |
| Water | 90.99 | 88.49 | 85.99 | 83.49 | 80.99 | 90.71 | 89.86 | 85.33 |
| Keltrol RL (Xanthan Gum) | 0.05 | 0.05 | 0.05 | 0.05 | 0.05 | 0.05 | 0.05 | 0.05 |
| Glycerin | 5.0 | 5.0 | 5.0 | 5.0 | 5.0 | 5.0 | 5.0 | 5.0 |
| Glycolic acid, 70% | 2.0 | 4.00 | 6.00 | 8.00 | 10.00 | 0 | 0 | 4.28 |
| Sodium Octane Sulfonate, 36% | 0 | 0 | 0 | 0 | 0 | 2.78 | 0 | 2.78 |
| Sodium Lauryl Sulfonate, 30% | 0 | 0 | 0 | 0 | 0 | 0 | 3.33 | 0 |
| Witconate AOS, 40% | 1.25 | 1.25 | 1.25 | 1.25 | 1.25 | 1.25 | 1.25 | 1.25 |
| Neodol 91-8 | 0.20 | 0.20 | 0.20 | 0.20 | 0.20 | 0.20 | 0.50 | 0.2 |
| FD&C #1 Blue | 0.008 | 0.008 | 0.008 | 0.008 | 0.008 | 0.008 | 0.008 | 0.008 |
| Sodium hydroxide, 50% | 0.5 | 1.00 | 1.50 | 2.00 | 2.50 | 0.0 | 0.0 | 1.10 |
| Micro Test: EN 1656, 15 second contact time @ 25° C.; Results are in log reduction from initial Bacteria Count 10⁷ cfu/mL | | | | | | | | |
| Staphyloccocus aureus | 3.95 | 4.20 | 4.28 | 4.46 | 4.50 | 0.11 | 0.07 | 6.53 |
| Escherichia coli | 1.08 | 1.15 | 1.23 | 1.54 | 2.02 | 1.20 | 1.20 | 6.67 |

The results in Table VI demonstrate that both glycolic acid and an anionic surfactant, such as sodium octane sulfonate or sodium lauryl sulfate, are required to obtain maximum antimicrobial efficacy, i.e., at least a 5 log reduction in all types of bacteria tested. Specifically, Formulations A-E demonstrate that formulations comprising glycolic acid but no sodium octane sulfonate or sodium lauryl sulfate do not exhibit maximum antimicrobial efficacy, even at increased levels of glycolic acid. Further, formulations F and G demonstrate that formulations comprising sodium octane sulfonate or sodium lauryl sulfate but no glycolic acid do not exhibit maximum antimicrobial efficacy, while formulation H, which comprises both glycolic acid and sodium octane sulfonate, does. These results demonstrate the synergistic antimicrobial effect achieved in a composition comprising glycolic acid, an anionic surfactant, e.g., sodium octane sulfonate, and a nonionic surfactant, e.g., an alcohol ethoxylate.

Example 6

Antimicrobial Activity of Formulations Having Varying Concentrations of Surfactants and Glycolic Acid In this Example, a series of formulations were tested for antimicrobial efficacy having varying concentrations of glycolic acid, Neodol 91-8, and Witconate AOS. The formulations were subjected to the EN 1656 test as described above in Example 1. The results appear in Table VII below.

TABLE VII

Formulations with Varying Concentrations of Surfactants and Glycolic Acid

| Ingredients and Concentration (% w/w) | A | B | C | D | E | F | G |
|---|---|---|---|---|---|---|---|
| Water | 86.78 | 85.33 | 86.05 | 86.76 | 85.43 | 85.58 | 86.08 |
| Keltrol RL (Xanthan Gum) | 0.05 | 0.05 | 0.05 | 0.05 | 0.05 | 0.05 | 0.05 |
| Glycerin | 5.00 | 5.00 | 5.00 | 5.00 | 5.00 | 5.00 | 5.00 |
| Glycolic acid, 70% | 4.28 | 4.28 | 3.57 | 2.86 | 4.28 | 4.28 | 4.28 |
| Sodium Octane Sulfonate, 36% | 2.78 | 2.78 | 2.78 | 2.78 | 2.78 | 2.78 | 2.78 |
| Witconate AOS, 40% | 0.0 | 1.25 | 1.25 | 1.25 | 1.25 | 1.00 | 0.50 |
| Neadol 91-8 | 0.00 | 0.00 | 0.20 | 0.20 | 0.10 | 0.20 | 0.20 |
| FD&C #1 Blue | 0.008 | 0.008 | 0.008 | 0.008 | 0.008 | 0.008 | 0.008 |
| Sodium hydroxide, 50% | 1.10 | 1.10 | 1.10 | 1.10 | 1.10 | 1.10 | 1.10 |
| Surfonic L12-8 | 0.00 | 0.20 | 0.00 | 0.00 | 0.00 | 0.00 | 0.00 |
| Micro Test: EN 1656, 15 second contact time@ 25° C.; Results are in log reduction from initial Bacteria Count $10^7$ cfu/mL | | | | | | | |
| *Staphyloccocus aureus* | 1.35 | 5.85 | 5.99 | 5.65 | 5.64 | 6.73 | 4.91 |
| *Escherichia coli* | 5.89 | 6.76 | 6.76 | 6.76 | 6.76 | 6.76 | 6.76 |

The results from Table VII demonstrate that all formulations tested showed greater than a 5 log reduction against *E. coli*. Formulation A, having sodium octane sulfonate and glycolic acid without an additional anionic or nonionic surfactant did not exhibit maximum antimicrobial efficacy. Formulation B, having glycolic acid, sodium octane sulfonate, Witconate AOS, and Surfonic L12-8, a $C_8$-$C_{10}$ alcohol with an average of approximately 6 or 8 moles of ethylene oxide per mole of alcohol, exhibited maximum antimicrobial efficacy. The CAS # for Surfonic L12-8 is 66455-15-0. Formulations C and D, having smaller amounts of glycolic acid (2.5 and 20 wt. %, respectively) exhibited maximum antimicrobial efficacy; although neither formulation exhibited a full log reduction of *S. aureus* (6.73 log reduction). Formulation E, having 0.10 wt. % of the nonionic surfactant Neodol 91-8 exhibited maximum antimicrobial efficacy, although it did not exhibit a full log reduction of *S. aureus* (6.73 log reduction). Formulation G demonstrates that a formulation having 0.2 wt. % Witconate AOS, glycolic acid, sodium octane sulfonate, and Neodol 91-8 does not exhibit maximum antimicrobial efficacy, while the same formulation with 0.4 wt. % Witconate AOS (Formulation F) does exhibit maximum antimicrobial efficacy.

Example 7

Antimicrobial Activity of Barrier Formulations Having Sodium Octane Sulfonate and Varying Concentrations of Sorbitol and Glycerin In this Example, a series of barrier formulations were tested for antimicrobial efficacy having sodium octane sulfonate and varying concentrations of sorbitol and glycerin. The formulations were subjected to the EN 1656 test as described above in Example 1. The results appear in Table VIII below.

TABLE VIII

Barrier Formulations with Sodium Octane Sulfonate and Various Concentrations of the Emollients: Glycerin and Sorbitol

| Ingredients and Concentration (% w/w) | A | B | C | D |
|---|---|---|---|---|
| Water | 79.67 | 77.53 | 78.39 | 76.67 |
| Keltrol RL (Xanthan Gum) | 0.40 | 0.40 | 0.40 | 0.40 |
| Pullulan | 0.30 | 0.30 | 0.30 | 0.30 |
| Glycerin | 10.00 | 5.00 | 7.00 | 3.00 |
| Sorbitol, 70% | 0.00 | 7.14 | 4.29 | 10.00 |
| Glycolic acid, 70% | 4.28 | 4.28 | 4.28 | 4.28 |
| Sodium Octane Sulfonate, 36% | 2.78 | 2.78 | 2.78 | 2.78 |
| Witconate AOS, 40% | 1.25 | 1.25 | 1.25 | 1.25 |
| Neodol 91-8 | 0.20 | 0.20 | 0.20 | 0.20 |
| FD&C #1 Blue | 0.016 | 0.016 | 0.016 | 0.016 |
| Sodium hydroxide, 50% | 1.10 | 1.10 | 1.10 | 1.10 |
| Micro Test: EN 1656, 15 second contact time@ 25° C.; Results are in log reduction from initial Bacteria Count $10^7$ cfu/mL | | | | |
| *Staphyloccocus aureus* | 6.5 | 6.5 | 6.5 | 6.5 |
| *Escherichia coli* | 6.54 | 6.54 | 6.54 | 6.54 |
| *Strep uberis* | 6.43 | 6.43 | 6.43 | 6.43 |
| *Pseudomonas aeruginosa* | 6.31 | 6.31 | 6.31 | 6.31 |

TABLE VIII-continued

Barrier Formulations with Sodium Octane Sulfonate and Various Concentrations of the Emollients: Glycerin and Sorbitol

| Ingredients and Concentration | Formulations | | | |
|---|---|---|---|---|
| (% w/w) | A | B | C | D |
| Streptococcus dysgalactiae | 6.41 | 6.41 | 6.41 | 6.41 |
| Streptococcus agalactiae | 6.4 | 6.4 | 6.4 | 6.4 |

The results in Table VIII demonstrate that variations in the ratio of the emollients, sorbitol and glycerin, present in the tested formulations does not adversely affect the antimicrobial efficacy of these formulations, as formulations A-D all exhibited maximum antimicrobial efficacy.

Example 8

Antimicrobial Activity of Barrier Formulations Having Sodium Lauryl Sulfate and Varying Concentrations of Sorbitol and Glycerin In this Example, a series of barrier formulations were tested for antimicrobial efficacy having sodium lauryl sulfate and varying concentrations of sorbitol and glycerin. The formulations were subjected to the EN 1656 test as described above in Example 1. The results appear in Table IX below.

TABLE IX

Barrier Formulations with Sodium Lauryl Sulfate and Various Concentrations of the Emollients: Glycerin and Sorbitol

| Ingredients and Concentration | Formulations | | |
|---|---|---|---|
| (% w/w) | A | B | C |
| Water | 79.12 | 77.54 | 76.67 |
| Keltrol RL (Xanthan Gum) | 0.40 | 0.40 | 0.40 |
| Pullulan | 0.30 | 0.30 | 0.30 |
| Glycerin | 10.0 | 7.00 | 5.00 |
| Sorbitol, 70% | 0.00 | 4.28 | 7.14 |
| Glycolic acid, 70% | 4.28 | 4.28 | 4.28 |
| Sodium Lauryl Sulfate, 30% | 3.33 | 3.33 | 3.33 |
| Witconate AOS, 40% | 1.25 | 1.25 | 1.25 |
| Neodol 91-8 | 0.20 | 0.50 | 0.50 |
| FD&C #1 Blue | 0.016 | 0.016 | 0.016 |
| Sodium hydroxide, 50% | 1.10 | 1.10 | 1.10 |
| Micro Test EN 1656, 15 second contact time@ 25° C.; Results are in log reduction from initial Bacteria Count $10^7$ cfu/mL | | | |
| Staphyloccocus aureus | 6.5 | 6.5 | 6.5 |
| Escherichia coli | 6.54 | 6.54 | 6.54 |
| Strep uberis | 6.43 | 6.43 | 6.43 |
| Pseudomonas aeruginosa | 6.31 | 6.31 | 6.31 |
| Streptococcus dysgalactiae | 6.41 | 6.41 | 6.41 |
| Streptococcus agalactiae | 6.4 | 6.4 | 6.4 |

The results in Table IX demonstrate that variations in the ratio of the emollients, sorbitol and glycerin, in the tested formulations do not adversely affect the antimicrobial efficacy, as these formulations exhibited maximum antimicrobial efficacy.

Example 9

Antimicrobial Activity of Barrier Formulations with Glycolic Acid and Various Surfactants In this Example, a series of barrier formulations were tested for antimicrobial efficacy having glycolic acid and various surfactants. Natrosol 250H is a hydroxyethylcellulose commercialized by Ashland Corp. The formulations were subjected to the EN 1656 test as described above in Example 1. The results appear in Table X below.

TABLE X

Barrier Formulations with Glycolic Acid and Various Surfactants

| Ingredients and Concentration | Formulations | | | | |
|---|---|---|---|---|---|
| (% w/w) | A | B | C | D | E |
| Water | 79.15 | 77.72 | 78.47 | 76.65 | 79.47 |
| Keltrol RL (Xanthan Gum) | 0.40 | 0.40 | 0.40 | 0.4 | 0 |
| Natrosol 250H | 0.00 | 0.00 | 0.00 | 0.00 | 0.80 |
| Pullulan | 0.3 | 0.3 | 0.3 | 0.3 | 0 |
| Glycerin | 10.0 | 10.0 | 10.0 | 10 | 10 |
| Glycolic acid, 70% | 4.28 | 5.71 | 5.71 | 4.28 | 4.28 |
| Sodium Octane Sulfonate, 30% | 0 | 0 | 0 | 0 | 0 |
| Witconate AOS, 40% | 3.75 | 3.75 | 2.5 | 6.25 | 0 |
| Neodol 91-8 | 1 | 1 | 1.5 | 1 | 1.0 |
| Barlox 12 | 0 | 0 | 0 | 0.00 | 3.33 |
| FD&C #1 Blue | 0.016 | 0.016 | 0.016 | 0.016 | 0.016 |
| Sodium hydroxide, 50% | 1.1 | 1.1 | 1.1 | 1.1 | 1.1 |
| Micro Test: EN 1656, 15 second contact time@ 25° C.; Results are in log reduction from initial Bacteria Count $10^7$ cfu/mL | | | | | |
| Staphyloccocus aureus | 6.22 | 6.22 | 6.22 | 6.37 | 1.88 |
| Escherichia coli | 1.53 | 1.91 | 2.31 | 5.01 | 3.32 |

The results in Table X demonstrate that maximum antimicrobial efficacy, i.e., at least a 5-log reduction in all types of bacteria tested, cannot be obtained in barrier formulations having glycolic acid and the above tested nonionic, cationic, and anionic surfactants at the above listed concentrations without the inclusion of sodium octane sulfonate.

Example 10

Antimicrobial Activity of Teat Dips Containing Sodium Octane Sulfonate, α-Olefin Sulfonate, and Glycolic Acid In this Example, the concentrations of SOS, AOS, and glycolic acid were varied in order to establish target amounts of each component required to provide maximum germicidal efficacy. The antimicrobial efficacy was tested according to EN1656 performed as described above in Example 1. The microorganisms tested were S. aureus (ATCC 6538) and E. coli (ATCC 10536). Antimicrobial activity of greater than a 5-log reduction was deemed acceptable. The results of this testing are given in Table XI.

TABLE XI

Teat Dips Containing Sodium Octane Sulfonate, α-Olefin Sulfonate, and Glycolic Acid

| Ingredients (% w/w) | A | | B | | C | | D | | E | |
|---|---|---|---|---|---|---|---|---|---|---|
| Water | 86.87 | 90.54 | 87.68 | 91.09 | 88.70 | 91.74 | 86.18 | 90.04 | 86.43 | 90.14 |
| Keltrol RD | 0.05 | 0.05 | 0.05 | 0.05 | 0.05 | 0.05 | 0.05 | 0.05 | 0.05 | 0.05 |
| Glycerin | 5.00 | 5.00 | 5.00 | 5.00 | 5.00 | 5.00 | 5.00 | 5.00 | 5.00 | 5.00 |
| SOS, 36% | 2.78 | 1.00 | 2.78 | 1.00 | 2.78 | 1.00 | 2.78 | 1.00 | 2.78 | 1.00 |
| AOS-40% | 0.63 | 0.25 | 0.63 | 0.25 | 0.63 | 0.25 | 0.50 | 0.20 | 0.25 | 0.10 |
| Neodol 91-8 | 0.20 | 0.20 | 0.20 | 0.20 | 0.20 | 0.20 | 0.20 | 0.20 | 0.20 | 0.20 |
| Glycolic Acid, 70% | 3.57 | 2.50 | 2.86 | 2.00 | 2.14 | 1.50 | 4.29 | 3.00 | 4.29 | 3.00 |
| FD&C blue | 0.008 | 0.008 | 0.008 | 0.008 | 0.008 | 0.008 | 0.008 | 0.008 | 0.008 | 0.008 |
| NaOH, 50% | 0.90 | 0.45 | 0.80 | 0.40 | 0.50 | 0.25 | 1.00 | 0.50 | 1.00 | 0.50 |

Teat Dips Containing Sodium Octane Sulfonate, α-Olefin Sulfonate, and Glycolic Acid

| Ingredients (% w/w) | F | | G | | H | | I | |
|---|---|---|---|---|---|---|---|---|
| Water | 86.01 | 89.49 | 86.21 | 89.49 | 84.25 | 88.79 | 85.89 | 89.39 |
| Keltrol RD | 0.05 | 0.05 | 0.05 | 0.05 | 0.05 | 0.05 | 0.05 | 0.05 |
| Glycerin | 5.00 | 5.00 | 5.00 | 5.00 | 5.00 | 5.00 | 5.00 | 5.00 |
| SOS, 36% | 1.39 | 0.50 | 0.69 | 0.25 | 2.78 | 1.00 | 1.39 | 0.50 |
| AOS-40% | 0.63 | 0.25 | 0.63 | 0.25 | 0.50 | 0.20 | 0.25 | 0.10 |
| Neodol 91-8 | 0.20 | 0.20 | 0.20 | 0.20 | 0.20 | 0.20 | 0.20 | 0.20 |
| Glycolic Acid, 70% | 5.71 | 4.00 | 5.71 | 4.00 | 5.71 | 4.00 | 5.71 | 4.00 |
| FD&C blue | 0.008 | 0.008 | 0.008 | 0.008 | 0.008 | 0.008 | 0.008 | 0.008 |
| NaOH, 50% | 1.00 | 0.50 | 1.50 | 0.75 | 1.50 | 0.75 | 1.50 | 0.75 |

Micro Test EN 1656, 15 second contact time @ 25° C.; Results are in log reduction from intal bacteria count $10^7$ cfu/mL

| | | | | | | | | | | |
|---|---|---|---|---|---|---|---|---|---|---|
| S. aureus | 6.6 | 6.6 | 6.6 | 6.6 | 6.6 | 5.2 | 4.1 | 6.6 | 5.1 | |
| E. coli | 6.6 | 6.6 | 6.6 | 6.6 | 6.6 | 4.1 | 2.1 | 3.8 | 4.4 | |

| Ingredients (% w/w)* | J | | K | | L | | M | |
|---|---|---|---|---|---|---|---|---|
| Water | 87.44 | 90.74 | 86.55 | 90.19 | 86.98 | 90.34 | 87.11 | 90.39 |
| Keltrol RL | 0.05 | 0.05 | 0.05 | 0.05 | 0.05 | 0.05 | 0.05 | 0.05 |
| Glycerin | 5.00 | 5.00 | 5.00 | 5.00 | 5.00 | 5.00 | 5.00 | 5.00 |
| SOS, 36% | 1.39 | 0.25 | 2.78 | 1.00 | 2.22 | 0.80 | 2.22 | 0.80 |
| AOS-40% | 0.63 | 0.25 | 0.13 | 0.05 | 0.25 | 0.10 | 0.13 | 0.05 |
| Neodol 91-8 | 0.20 | 0.20 | 0.20 | 0.20 | 0.20 | 0.20 | 0.20 | 0.20 |
| Glycolic Acid, 70% | 4.29 | 3.00 | 4.29 | 3.00 | 4.29 | 3.00 | 4.29 | 3.00 |
| FD&C blue | 0.008 | 0.01 | 0.008 | 0.008 | 0.008 | 0.008 | 0.008 | 0.008 |
| NaOH, 50% | 1.00 | 0.50 | 1.00 | 0.50 | 1.00 | 0.50 | 1.00 | 0.50 |

| Ingredients (% w/w)* | N | | O | | P | | Q | |
|---|---|---|---|---|---|---|---|---|
| Water | 87.66 | 90.59 | 89.61 | 92.34 | 90.42 | 92.89 | 88.14 | 90.74 |
| Keltrol RL | 0.05 | 0.05 | 0.05 | 0.05 | 0.05 | 0.05 | 0.05 | 0.05 |
| Glycerin | 5.00 | 5.00 | 5.00 | 5.00 | 5.00 | 5.00 | 5.00 | 5.00 |
| SOS, 36% | 1.67 | 0.60 | 2.78 | 1.00 | 2.78 | 1.00 | 0.69 | 0.25 |
| AOS-40% | 0.13 | 0.05 | 0.63 | 0.25 | 0.63 | 0.25 | 0.63 | 0.25 |
| Neodol 91-8 | 0.20 | 0.20 | 0.20 | 0.20 | 0.20 | 0.20 | 0.20 | 0.20 |
| Glycolic Acid, 70% | 4.29 | 3.00 | 1.43 | 1.00 | 0.71 | 0.50 | 4.29 | 3.00 |
| FD&C blue | 0.008 | 0.008 | 0.008 | 0.008 | 0.008 | 0.008 | 0.008 | 0.008 |
| NaOH, 50% | 1.00 | 0.50 | 0.30 | 0.15 | 0.20 | 0.10 | 1.00 | 0.50 |

Micro Test: EN 1656, 15 second contact time @ 25° C.; Results are in log reduction from initial bacteria count $10^7$ cfu/mL

| | | | | | | | | |
|---|---|---|---|---|---|---|---|---|
| S. aureus | 5.4 | 6.63 | 6.63 | 6.63 | 4.60 | 6.63 | 6.63 | 4.03 |
| E. coli | 5.0 | 6.86 | 6.86 | 6.86 | 6.86 | 6.86 | 4.61 | 2.42 |

The data demonstrates that the germicidal efficacy decreases as SOS concentration decreases. Below an SOS concentration of 0.5%, the composition does not provide acceptable levels of germicidal efficacy. Germicidal efficacy is also dependent upon glycolic acid concentration. Below a glycolic acid concentration of 0.5%, the germicidal efficacy drops below acceptable levels for E. coli. A decrease in germicidal efficacy was also observed when total surfactant concentration (SOS, AOS and Neodol) dropped below 1.0%.

Example 11

Antimicrobial Activity of Teat Dips and Barrier Teat Dip Containing Sodium Octane Sulfonate, α-Olefin Sulfonate, and Glycolic Acid In this Example, the germicidal efficacy of various teat dips and a barrier teat dip was determined. The level of AOS employed was varied slightly among the teat dip formulations. Germicidal efficacy was determined under the modified EN 1656 micro test described in Example 1. The results of this testing are presented in Table XII.

TABLE XII

Teat Dips Containing Sodium Octane Sulfonate, α-Olefin Sulfonate, and Glycolic Acid

| Ingredients and Concentration (% w/w) | Teat Dip A | Teat Dip B | Teat Dip C | Teat Dip D | Barrier Teat Dip |
|---|---|---|---|---|---|
| Water | 86.05 | 85.76 | 85.88 | 85.97 | 78.06 |
| Glycerin, 99.7% (non-animal origin) | 5.0 | 5.0 | 5.0 | 5.0 | 5.00 |
| Keltrol RL | 0.05 | 0.05 | 0.05 | 0.05 | 0.40 |
| PVP K-30 | — | — | — | — | 0.50 |
| Sorbitol, 70% | — | — | — | — | 7.14 |
| SOS, 36% | 2.78 | 2.78 | 2.78 | 2.78 | 2.78 |
| AOS, 40% - Bioterge AS40K | 0.63 | 0.82 | 0.70 | 0.61 | 0.63 |
| Neodol 91-8 | 0.20 | 0.20 | 0.20 | 0.20 | 0.20 |
| Glycolic Acid, 70% | 4.28 | 4.28 | 4.28 | 4.28 | 4.28 |
| FD&C Blue #1 | 0.008 | 0.008 | 0.008 | 0.008 | 0.01 |
| Sodium hydroxide, FCC, 50% | 1.00 | 1.10 | 1.10 | 1.10 | 1.00 |
| Micro Test: EN 1656, 15 second contact time@ 25° C.; Results are in log reduction from initial bacteria count $10^7$ cfu/mL | | | | | |
| E. Coli | 6.7 | 6.7 | 6.7 | 6.7 | 6.7 |
| S. aureus | 6.5 | 6.5 | 6.5 | 6.5 | 6.5 |
| P. aeruginosa | 6.2 | 6.2 | 6.2 | 6.2 | 6.2 |
| S. uberis | 6.5 | 6.5 | 6.5 | 6.5 | 6.5 |
| S. agalactia | 6.5 | 6.5 | 6.5 | 6.5 | 6.5 |
| S. dysgalactiae | 6.4 | 6.4 | 6.4 | 6.4 | 6.4 |
| pH | 3.20-3.40 | | | | 3.20-3.40 |
| Specific Gravity @ 25° C. | 1.02-1.04 | | | | 1.04-1.06 |
| Freezing Point, ° C. | 0 | | | | 0 |
| Viscosity @ 25° C., cps (LV, Spindle 1, 100 rpm) | 8-15* | | | | 500-650** |
| Appearance | Clear blue liquid | | | | Clear blue liquid |

*LV Viscometer, spindle #1, 100 rpm
**LV Viscometer, spindle #2, 30 rpm

All formulations from Table XII provided complete kill of the various microorganisms within 15 seconds.

Example 12

Antimicrobial Activity of Formulations Comprising Sodium Lauryl Sulfate

In this Example, compositions comprising sodium lauryl sulfate (SLS) were formulated and their germicidal efficacy. The antimicrobial efficacy was tested according to EN1656 performed as described above in Example 1. The microorganisms tested were S. aureus (ATCC 6538) and E. coli (ATCC 10536). Antimicrobial activity of greater than a 5-log reduction was deemed acceptable. Formulation E was formulated without any surfactants for comparative purposes, illustrating the effect of glycolic acid alone on germicidal efficacy. The results of this testing are given in Table XIII.

TABLE XIII

Teat Dips Containing Sodium Lauryl Sulfate, α-Olefin Sulfonate, and Glycolic Acid

| Ingredients (% w/w)* | A | | B | | C | | D | | E | |
|---|---|---|---|---|---|---|---|---|---|---|
| Water | 85.49 | 89.99 | 87.16 | 90.49 | 87.99 | 90.74 | 87.54 | 90.64 | 89.65 | 91.44 |
| Keltrol RD | 0.05 | 0.05 | 0.05 | 0.05 | 0.05 | 0.05 | 0.05 | 0.05 | 0.05 | 0.05 |
| Glycerin | 5.00 | 5.00 | 5.00 | 5.00 | 5.00 | 5.00 | 5.00 | 5.00 | 5.00 | 5.00 |
| SLS, 30% | 3.33 | 1.00 | 1.67 | 0.50 | 0.83 | 0.25 | 1.67 | 0.50 | 0.00 | 0.00 |
| AOS-40% | 0.63 | 0.25 | 0.63 | 0.25 | 0.63 | 0.25 | 0.25 | 0.10 | 0.00 | 0.00 |
| Neadcl 91-8 | 0.20 | 0.20 | 0.20 | 0.20 | 0.20 | 0.20 | 0.20 | 0.20 | 0.00 | 0.00 |
| Glycolic Acid, 70% | 4.29 | 3.00 | 4.29 | 3.00 | 4.29 | 3.00 | 4.29 | 3.00 | 4.29 | 3.00 |
| FD&C blue | 0.008 | 0.008 | 0.008 | 0.008 | 0.008 | 0.008 | 0.008 | 0.008 | 0.008 | 0.008 |
| NaOH, 50% | 1.00 | 0.50 | 1.00 | 0.50 | 1.00 | 0.50 | 1.00 | 0.50 | 1.00 | 0.50 |

Formulations (first column based on ingredients, second column based on absolute content)

TABLE XIII-continued

Micro Test: EN 1656, 15 second contact time@ 25° C.; Results are in log reduction from initial bacteria count $10^7$ cfu/mL

| E. coli | 4.83 | 4.42 | 4.16 | 4.28 | 2.29 |
|---|---|---|---|---|---|
| S. aureus | 6.64 | 5.39 | 5.12 | 5.12 | 1.32 |

All of the SLS-containing formulations tested exhibited greater than a 5-log reduction for S. aureus. However, none of the formulations met this same level of performance for E. coli. These results are in contrast with the results identified in Table IV, and in particular Formulations C and D. Both Formulations C and D from Table IV exhibited acceptable antimicrobial efficacy for both pathogens tested. Formulation C from Table IV utilized approximately twice the level of AOS (and Formulation D approximately six times the level of AOS) than any of the formulations listed in Table XIII. Thus, a decline in antimicrobial efficacy is observed when AOS values drop to 0.25% w/w (absolute) when SLS is employed at 1% w/w (absolute). Formulation E illustrates the antimicrobial efficacy of the composition without any SLS, AOS, or Neodol 91-8 (i.e., when glycolic acid alone is present at 3% w/w absolute). The composition performs quite poorly, illustrating the criticality of the surfactants.

Example 13

Antimicrobial Activity of Compositions Comprising Glycolic Acid and One Surfactant In this Example, the antimicrobial efficacy of certain formulations prepared with just one of sodium octane sulfonate (SOS), α-olefin sulfonate (AOS), or Neodol 91-8 was determined. The antimicrobial efficacy was tested according to EN1656 performed as described above in Example 1. The microorganisms tested were S. aureus (ATCC 6538) and E. coli (ATCC 10536). Antimicrobial activity of greater than a 5-log reduction was deemed acceptable. The results are given in Table XIV.

TABLE IV

Teat Dips Containing Glycolic Acid and One Surfactant

| Ingredients (% w/w) | Formulations (first column based on ingredients, second column based on absolute content) | | | | | |
|---|---|---|---|---|---|---|
| | A | | B | | C | |
| Water | 86.87 | 90.44 | 89.03 | 91.19 | 89.45 | 91.24 |
| Keltrol RD | 0.05 | 0.05 | 0.05 | 0.05 | 0.05 | 0.05 |
| Glycerin | 5.00 | 5.00 | 5.00 | 5.00 | 5.00 | 5.00 |
| SOS, 36% | 2.78 | 1.00 | 0.00 | 0.00 | 0.00 | 0.00 |
| AOS-40% | 0.00 | 0.00 | 0.63 | 0.25 | 0.00 | 0.00 |
| Neodol 91-8 | 0.00 | 0.00 | 0.00 | 0.00 | 0.20 | 0.20 |
| Glycolic Acid, 70% | 4.29 | 3.00 | 4.29 | 3.00 | 4.29 | 3.00 |
| FD&C blue | 0.008 | 0.008 | 0.008 | 0.008 | 0.008 | 0.008 |
| NaOH, 50% | 1.00 | 0.50 | 1.00 | 0.50 | 1.00 | 0.50 |

Micro Test: EN 1656, 15 second contact time@ 25° C.; Results are in log reduction from initial bacteria count $10^7$ cfu/mL

| E. coli | 6.42 | 6.42 | 3.13 |
|---|---|---|---|
| S. aureus | 4.16 | 2.52 | 1.36 |

Each of Formulations A-C is based upon Formulation A from Table XII, which contains each of the surfactants in the individual amounts employed in this Example. The antimicrobial efficacy of Formulations A-C may be directly compared with the antimicrobial efficacy of Formulation A from Table XII. The formulations of this Example do not exhibit acceptable results for all tested pathogens. While Formulations A and B show greater than a 6-log reduction for E. coli, neither formulation performs suitably for S. aureus. However, as evidenced by the results given in Table XII, when all three surfactants are brought together, the formulation surprisingly results in a complete kill of S. aureus and E. coli.

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

Claims Not Limited To Disclosed Embodiments

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

The invention claimed is:

1. An antimicrobial composition comprising:
   glycolic acid as the only organic acid present in said composition;
   sodium octane sulfonate or sodium lauryl sulfate;
   a C9-C11 alcohol ethoxylate surfactant; and
   at least one additional anionic surfactant, wherein said at least one additional anionic surfactant comprises a C14-C16 alpha-olefin sulfonate, and
   wherein said composition is characterized by a Lysis/Denaturation (L/D) ratio greater than 100.

2. The composition according to claim 1, wherein the glycolic acid, sodium octane sulfonate or sodium lauryl sulfate, and the additional anionic surfactant are each present in an amount ranging from about 0.01 to 40 wt. %.

3. A method for controlling or preventing bovine mastitis comprising contacting the teats of a cow with a teat dip that comprises:
   glycolic acid as the only organic acid present in said composition;
   sodium octane sulfonate or sodium lauryl sulfate;
   a C9-C11 alcohol ethoxylate surfactant; and
   at least one additional anionic surfactant, wherein said at least one additional anionic surfactant comprises a C14-C16 alpha-olefin sulfonate,
   wherein said teat dip is characterized by a Lysis/Denaturation (L/D) ratio greater than 100.

4. The method according to claim 3, wherein the glycolic acid, sodium octane sulfonate or sodium lauryl sulfate, and the additional anionic surfactant are each present in an amount ranging from about 0.01 to 40 wt. %.

5. The composition according to claim 1, wherein the composition comprises from 0.5% to 10% by weight of glycolic acid.

6. The composition according to claim 1, wherein the composition comprises from 0.25% to 5% by weight of the sodium octane sulfonate or sodium lauryl sulfate.

7. The composition according to claim 1, wherein the composition comprises from 0.05% to 2% by weight of the C14-C16 alpha-olefin sulfonate.

8. The composition according to claim 1, wherein the composition comprises from 0.05% to 1% by weight of the C9-C11 alcohol ethoxylate surfactant.

9. The method according to claim 3, wherein the teat dip comprises from 0.5% to 10% by weight of glycolic acid.

10. The method according to claim 3, wherein the teat dip comprises from 0.25% to 5% by weight of the sodium octane sulfonate or sodium lauryl sulfate.

11. The method according to claim 3, wherein the teat dip comprises from 0.05% to 2% by weight of the C14-C16 alpha-olefin sulfonate.

12. The method according to claim 3, wherein the teat dip comprises from 0.05% to 1% by weight of the C9-C11 alcohol ethoxylate surfactant.

* * * * *